United States Patent [19]

Yafuso et al.

[11] Patent Number: 5,508,509
[45] Date of Patent: Apr. 16, 1996

[54] SENSING ELEMENTS AND METHODS FOR UNIFORMLY MAKING INDIVIDUAL SENSING ELEMENTS

[75] Inventors: Masao Yafuso, Lake Forest, Calif.; Ronnie L. Pratt, Hammond, Wis.; Kathryn R. Bretscher, Shoreview; Kenneth B. Wood, St. Paul, both of Minn.; John L. Dektar, Laguna Hills, Calif.; James G. Bentsen, North St. Paul, Minn.

[73] Assignee: Minnesota Mining and Manufacturing Company, St. Paul, Minn.

[21] Appl. No.: 159,799

[22] Filed: Nov. 30, 1993

[51] Int. Cl.⁶ ................................................. G01N 33/50
[52] U.S. Cl. .................... 250/216; 422/82.05; 422/91; 436/68; 436/136; 128/634
[58] Field of Search .................... 250/216, 227.11, 250/227.14, 227.21; 128/634; 435/7.7, 7.24, 7.32, 7.4, 7.71, 7.72, 7.92, 805, 963, 968, 970, 971; 422/56, 57, 88, 91, 79, 82.05, 82.07, 82.08, 83, 88, 91; 436/68, 136

[56] References Cited

U.S. PATENT DOCUMENTS

| | | | |
|---|---|---|---|
| Re. 31,879 | 5/1985 | Lübbers et al. | 436/133 |
| 4,225,410 | 9/1980 | Pace | 204/195 R |
| 4,363,874 | 12/1982 | Greenquist | 435/7.7 |
| 4,510,094 | 4/1985 | Drahnak | 260/429 CY |
| 4,530,879 | 7/1985 | Drahnak | 428/352 |
| 4,557,900 | 12/1985 | Heitzmann | 422/55 |
| 4,600,484 | 7/1986 | Drahnak | 204/157.74 |
| 4,640,820 | 2/1987 | Cooper | 422/68 |
| 4,824,789 | 4/1989 | Yafuso et al. | 436/68 |
| 4,849,172 | 7/1989 | Yafuso et al. | 422/55 |
| 4,889,613 | 12/1989 | McNeal et al. | 204/416 |
| 4,916,169 | 4/1990 | Boardman et al. | 522/27 |
| 4,989,606 | 2/1991 | Gehrich et al. | 128/637 |
| 5,204,219 | 4/1993 | Van Ooij et al. | 430/272 |
| 5,246,109 | 9/1993 | Markle et al. | 206/363 |
| 5,298,741 | 3/1994 | Walt et al. | 250/227.21 |
| 5,338,430 | 8/1994 | Parsonage et al. | 204/412 |
| 5,349,181 | 9/1994 | Saini et al. | 250/227.14 |

Primary Examiner—Edward P. Westin
Assistant Examiner—John R. Lee
Attorney, Agent, or Firm—Gary L. Griswold; Walter N. Kirn; F. Andrew Ubel

[57] ABSTRACT

Sensing elements, useful in sensing the concentration of a gas, e.g., carbon dioxide, in a medium, e.g. blood, and methods for making such sensing elements are disclosed. In one embodiment, the method comprises continuously placing a sensing composition precursor in contact with a continuous web, forming a continuous sensing composition from the precursor, and applying a continuous opaque film to the sensing composition. A plurality of individual sensing elements are formed from this composite structure. These sensing elements, which each have very similar sensing characteristics, are placed in a sensor fixture for use.

58 Claims, 4 Drawing Sheets

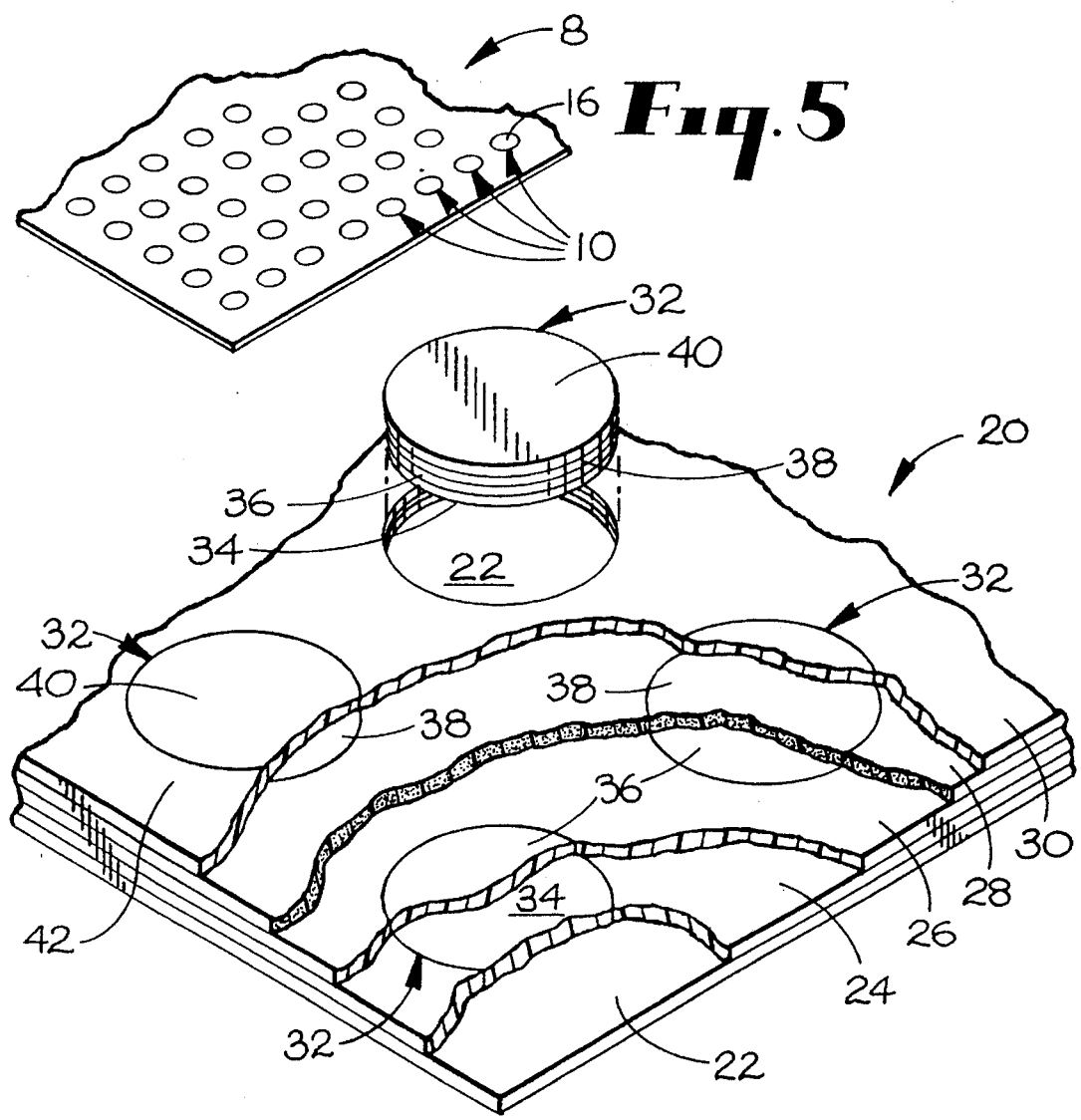
Fig.5
Fig.7
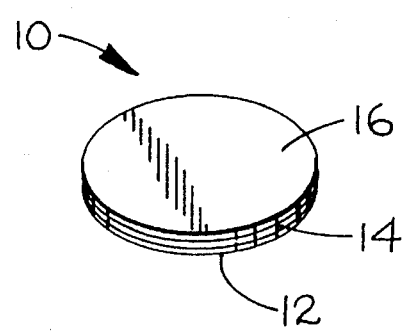
Fig.6

SENSING ELEMENTS AND METHODS FOR UNIFORMLY MAKING INDIVIDUAL SENSING ELEMENTS

FIELD OF THE INVENTION

This invention is related to sensing elements useful in sensing an analyte of interest, and to methods for making such sensing elements. More particularly, the invention relates to sensing elements and to methods for "mass producing" sensing elements, for example, useful in sensing the concentration of a gas, such as, carbon dioxide, oxygen and the like, in an aqueous medium, for example, blood.

BACKGROUND OF THE INVENTION

In many situations, it is useful to determine the concentration, e.g. partial pressure, of a gas in a medium, e.g., a fluid medium. One such situation is the determination of the concentration of gas, e.g., carbon dioxide, oxygen and the like, in blood. Fluorescence-based sensors have been utilized to accomplish real time blood gas sensing. For example, fluorescence-based sensors can be used in an extracorporeal blood loop as shown in Cooper U.S. Pat. No. 4,640,820 and in vivo as disclosed in Lubbers et al U.S. Pat. No. Re. 31,879. Each of these patents is incorporated by reference in its entirety herein.

Yafuso et al., U.S. Pat. No. 4,824,789 discloses a sensing composition and sensor useful for determining the concentration of a gas in blood. This patent discloses a sensing composition which is useful when placed on the optical surface of an optical fiber to form a sensor. The sensing composition comprises an aqueous first phase dispersed in a cross-linked polymeric second phase. The aqueous first phase includes a dye, for example a pH sensitive dye. The cross-linked polymeric second phase, which is gas permeable and ion impermeable, preferably is silicone-based and includes a hydrophobic filler, such as hydrophobic fumed silica particles. These sensing compositions may further include one or more emulsification enhancement agents, such as water soluble dextran and polyvinyl alcohol. This patent discloses that a teflon sleeve is used on the optical fiber during manufacture of the sensor to retain the sensing composition precursor on the optical surface of the optical fiber. The sensor also includes an opaque overcoat, such as cellulose impregnated with carbon black, to optically isolate the sensing composition.

The use of disposable cassettes for blood analysis is of substantial current interest, for example, to eliminate cross-patient contamination and to keep more expensive components, e.g., optical and electronic components, of the sensor system from being exposed directly to blood. One disposable cassette system is disclosed in U.S. Pat. No. 4,989,606.

Such a disposable cassette includes an indent, well or cavity into which a sensing element is at least partially placed. The sensing element is exposed to blood and the sensing component, e.g., a fluorescent dye, gives off a signal which varies in response to variations in the concentration of the gas of interest in the blood. A signal transmitter, e.g., an optical fiber, spaced away from the cassette well and blood transmits this signal to a processor where it is analyzed to provide the desired blood gas concentration determination.

One problem which has presented itself with regard to the use of these cassettes is that the characteristics of the sensing elements vary significantly from one to another. Also, when the sensing element is manufactured or assembled in situ, for example, in the well of the cassette, there is no chance to screen the sensing element before it is secured to, for example, bonded to, the cassette. Thus, out-of-specification sensing elements can be included in the cassette and determined as being non-conforming only after the assembled cassette, which often includes a number of other sensing elements for different blood constituents, is tested. At this point, the entire cassette must be discarded, resulting in substantial waste and cost.

It would be clearly advantageous to provide new sensing elements and/or new methods for making sensing elements, particularly for use in such cassettes.

RELATED APPLICATIONS

Of related interest in U.S. patent application Ser. No. 08/160,687, filed on even date herewith by the assignee of this invention: "Sensor with Improved Drift Stability", now U.S. Pat. No. 5,403,746 and copending U.S. patent applications Ser. Nos. 08/136,967 now U.S. Pat. No. 5,462,879 "Emission Quenching Sensors" and 08/137,289 "Sensors and Methods for Sensing" now U.S. Pat. No. 5,409,666 which are herein incorporated by reference.

SUMMARY OF THE INVENTION

New sensing elements, and methods for making sensing elements, useful in sensing an analyte, such as a gas, for example, carbon dioxide, oxygen and the like, in a medium, for example, blood, have been discovered. The present sensing elements provide substantial benefits. For example, these elements can be produced so as to have substantially uniform characteristics, and then tested or screened to assure conformity to product specifications, before they are included in the final sensor holder or fixture. This feature reduces the cost and time required to produce high quality sensors which provide reliable and consistent analyte sensing results. In addition, the present sensing elements are preferably produced in a form which is very convenient to use when including individual sensing elements into sensor holders or fixtures. The present methods for producing sensing elements are straightforward, relatively easy to practice, and very effectively mass produce many sensing elements which have very similar, if not identical, sensing characteristics. The relative amount of out-of-specification sensing elements produced is reduced and, since the sensing elements can be tested or screened before being included with the other sensor components, the cost of producing out-of-specification sensing elements is even further reduced. Moreover, because of the substantial uniformity achieved in mass producing the present sensing elements, the amount of testing of sensing elements can be greatly reduced, thereby even further reducing costs without adversely impacting the quality of the final sensing elements.

In one broad aspect of the present invention, methods for making sensors adapted for sensing an analyte are provided. Such methods comprise placing, preferably continuously placing, a sensing composition precursor on a continuous web, and forming a sensing composition responsive to the analyte from the sensing composition precursor on the web. In a particularly useful embodiment, a continuous sensing composition is formed, from the sensing composition precursor included in the precursor-containing web, which is sized and structured to be dividable among a plurality of sensing elements. The continuous web preferably is made of a polymeric material. In one embodiment, the sensing composition precursor comprises a sensing component, which is responsive to the analyte of interest, and a polymer precursor. The above-noted forming step preferably involves polymerizing this polymer precursor, such as by employing a photo activated, for example, an ultraviolet light activated, polymerization catalyst component. The sensing composition is preferably useful in sensing the concentration of a gas, for example, carbon dioxide, oxygen and the like, in a medium, for example, an aqueous medium such as blood.

Continuously placing the sensing composition precursor on the continuous web provides substantial advantages. For example, it has been found that a substantially uniform coating of sensing composition precursor can be continuously placed on the web much more easily, controllably and reliably relative to placing the precursor on the web in a batch-type process, such as by coating relatively small individual sheets of the web material. Moreover, since very large numbers of individual sensing elements can be produced in a single "run" using this continuous processing, the almost inherent and disadvantageous variability from individual sheet to sheet obtained with batch-type processing is avoided. Also, adjustments can easily be made during the continuous processing, particularly early in the run, to provide that a sensing composition precursor/web of desired quality is achieved.

The continuous web is preferably treated or coated to enhance the adhesion of the sensing composition to the continuous web, for example, relative to the adhesion of the sensing composition to an identical continuous web which has not been so treated or coated. Such treatment may include one or more of the following: subjecting the continuous web to a plasma treatment, and subjecting the continuous web to a corona discharge treatment. The adhesion enhancing coating on the continuous web may comprise a primer agent or the like material.

In a further particularly useful embodiment, the present methods include forming or providing a continuous opaque film on the sensing composition, for example, so that the sensing composition is located between the continuous web and the opaque film. Alternately, the continuous web, noted above, can be a continuous opaque film. This opaque film can be formed prior to being associated with the sensing composition or it can be formed in situ on the sensing composition. The continuous opaque film is permeable to the analyte to be sensed. Such an opaque film is particularly useful in applications where the final sensing element derived from the continuous web/sensing composition composite structure is to be optically isolated, for example, to reduce reflection and/or other optical interferences so that more consistent sensing signals are provided and, ultimately, to promote or facilitate the accuracy of the sensor.

A further useful embodiment provides that the present methods include placing a continuous adhesive member or layer on the continuous web so that the continuous web is located between the continuous adhesive member and the sensing composition. The continuous adhesive member preferably includes an adhesive selected from pressure sensitive adhesive compositions. In a preferred embodiment, the continuous adhesive member includes an adhesive composition and a release membrane or liner in contact with the adhesive composition. The continuous adhesive member is placed so that the adhesive composition is in contact, preferably direct contact, with the continuous web. Alternatively, the sensing composition, noted above, can be a continuous adhesive member.

Once the sensing composition-containing continuous web is produced, a plurality of individual sensing elements can be formed, for example, cut, from this material. Each of the plurality of sensing elements includes a sensing composition layer (derived from the continuous sensing composition). Each of the sensing elements may include a web layer (derived from the continuous web) or may include no portion of the continuous web. For example, after the sensing composition-containing web is formed, the web can be physically stripped away, dissolved or otherwise removed from the sensing composition so that the sensing elements that are ultimately formed do not include a web portion or layer. In a useful embodiment, each of the sensing elements includes an opaque layer (derived from the continuous opaque film), a sensing composition layer (derived from the sensing composition located between the continuous web and the continuous opaque film) and a web layer (derived from the continuous web). Once the individual sensing elements are formed, each of such elements can be used by being secured, preferably adhesively secured, to a sensor holder or fixture, for example, in a cavity or indent of a sensor cassette.

If a continuous adhesive member is included in the sensing composition-containing web, each of the sensing elements produced therefrom includes a sensing composition layer, a web layer and an adhesive composition layer (derived from the continuous adhesive member), and preferably an opaque layer. It is preferred, if the release membrane is employed, that it remain substantially intact during the forming of the plurality of sensing elements. In this embodiment, after the individual sensing elements have been formed, non-sensing element material, that is material which is not included in any of the plurality of sensing elements produced, is preferably removed from the intact release membrane. The resulting structure, that is the intact release membrane or liner on which are located the plurality of individual sensing elements, is a particularly useful and convenient source of individual sensing elements. For example, one or more of the individual sensing elements can be chosen at random and tested to determine whether or not such individual sensing elements are within product specifications. If such specifications are met, because of the nature of the present methods of forming the individual gas sensing elements, one can be substantially assured that all the other individual sensing elements on the release membrane also meet product specifications and can be used without further testing. Having the individual sensing elements located on the release membrane very conveniently allows the individual sensing elements to be removed from the release membrane and placed in individual sensor fixtures, when desired. This, in turn, reduces the cost of producing the final sensor including the sensor element.

Sensing composition precursors, for example, including light activated polymerization catalyst components as described herein, are within the scope of the present invention. Sensing composition-containing webs are also included within the scope of the present invention. Such structures comprise a continuous web, and a continuous sensing composition responsive to the analyte to be sensed and located on the continuous web. The continuous web and continuous sensing composition are as described elsewhere herein. The present sensing composition-containing webs can be produced in accordance with the methods described herein. In addition, sources of individual sensing elements, for example, including continuous release membranes, and individual sensing elements, as described elsewhere herein, are included within the scope of the present invention.

After the individual sensing element has been produced, and it has been determined to meet product specifications, it is secured to a sensor holder or fixture, preferably at least partially in a cavity or well having an open end located in a sensor holder. The sensing element is preferably oriented so that the sensing composition is exposed to the medium being monitored. The sensor, comprising the sensing element, and sensor holder or fixture, is now ready for use in a sensing application, for example, monitoring the concentration of a gas in blood, as desired.

These and other aspects of the present invention are set forth in the following detailed description and claims, particularly when considered in conjunction with the accompanying drawings in which like parts bear like reference numerals.

BRIEF DESCRIPTION OF THE DRAWINGS

FIG. 5 is a partial top front view, in perspective, of one embodiment of a composite structure from which individual sensing elements are produced.

FIG. 6 is a top front view, in perspective, of an individual sensing element formed from the composite structure shown in FIG. 5.

FIG. 7 is a partial top front view, in perspective, of an alternate embodiment of a composite structure from which individual sensing elements are produced. This drawing shows a number of the composite layers broken away for illustrative clarity and, in addition, shows an individual sensing element produced from the composite structure.

Figure 1:
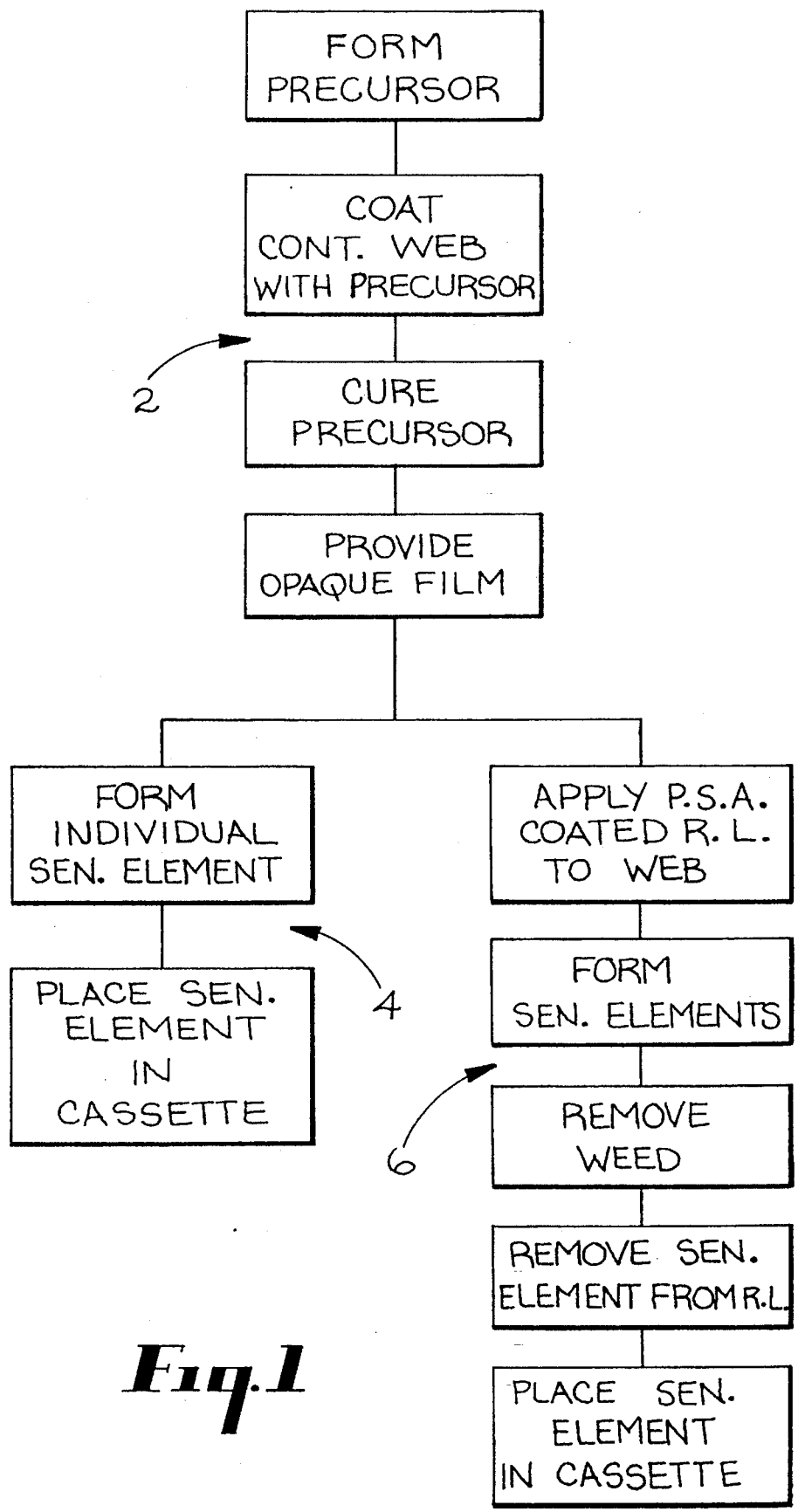
FIG. 1 is a block diagram illustrating two embodiments of the present methods of producing sensors.

In the drawings, no attempt has been made to present the individual layers of the composites and sensing elements as having different thicknesses. It should be understood, however, that such differences do exist, as described herein.

DETAILED DESCRIPTION OF THE INVENTION

In one important aspect, the present invention is directed to methods for producing sensors including individual sensing elements, such as individual gas sensing elements, for example, carbon dioxide sensing elements, oxygen sensing elements and the like, useful in sensing an analyte, such as a gas, in a fluid medium, such as blood.

The present methods of producing sensors are described with particular reference to FIG. 1, and the layered composites, composite structures and individual sensing elements formed are described with particular reference to FIGS. 5, 6 and 7.

The embodiments of the present methods for producing sensors illustrated in FIG. 1 comprise a series of steps, each step being represented by a different box in FIG. 1. Each of these steps is discussed in detail hereinafter. Briefly, however, these embodiments of the present methods involve the following steps. In an initial portion of the present methods, shown generally at 2 in FIG. 1, a sensing composition precursor is formed and placed, for example, coated, on a continuous web. A continuous sensing composition is formed from the precursor and is sized and structured to be dividable among a plurality of individual sensing elements. The sensing composition precursor often includes a polymer precursor which is cured, that is polymerized and/or cross-linked, in forming the continuous sensing composition. A continuous opaque film is placed, for example, applied, formed or the like, so that this film is located on the continuous sensing composition, and the sensing composition is positioned between the opaque film and the continuous web so that a continuous web/sensing composition/opaque film composite is formed. This composite is illustrated at 8 in FIG. 5. The individual sensing elements can be formed from composite 8, preferably using one of two alternate approaches.

In one embodiment illustrated generally at 4 in FIG. 1, the individual sensing elements are formed from the continuous web/sensing composition/opaque film composite 8. This forming may involve cutting or otherwise dividing the composite 8 to produce the individual sensing elements 10 each of which has a web layer 12 (derived from the continuous web), a sensing composition layer 14 (derived from the continuous sensing composition in the composite) and an opaque layer 16 (derived from the continuous opaque film). After testing and/or screening to determine that these individual sensing elements are satisfactory, for example, meet product specifications, these elements are secured to sensor holders or fixtures, for example, cavities or indents in sensor cassettes. The individual sensing elements, positioned as noted above, are ready for use.

In another embodiment illustrated generally at 6 in FIG. 1, an adhesive composition layer, including an adhesive composition, preferably comprising a pressure sensitive adhesive composition (PSA), is placed on the continuous web of the web/sensing composition/opaque film composite. This adhesive layer, which is located so that the continuous web is between the adhesive layer and the continuous sensing composition, is preferably located on a release liner. Thus, an additional composite, illustrated generally at 20 in FIG. 7, is formed in which the adhesive layer is located between the release liner and the continuous web. Thus, additional composite 20 includes release liner 22, adhesive layer 24, continuous web 26, continuous sensing composition 28 and continuous opaque film 30.

This additional composite 20 is "converted" to form individual sensing elements 32 located on the release liner 22. This "converting" or "individual sensing element forming" step is accomplished by cutting or otherwise dividing the additional composite 20 into individual sensing elements 32 located on the release liner 22, which remains intact during this step. Each of these individual sensing elements 32 includes an adhesive composition layer 34 (derived from adhesive layer 24), a web layer 36 (derived from continuous web 26), a sensing composition layer 38 (derived from continuous sensing composition 28) and an opaque layer 40 (derived from continuous opaque film 30). Material 42 which is not included in any of the sensing elements 32 is removed from the release liner 22. The remaining structure, that is the release liner 22 carrying individual sensing elements 32, is a very convenient source of individual sensing elements. Thus, after appropriate testing and/or screening to determine that the individual sensing elements 32 are of acceptable quality, they can be individually removed from the release liner 22 and secured to a sensor holder or fixture, for example, a cavity or indent in a sensor cassette, so that the adhesive layer is in contact with the sensor holder or fixture. In this manner, the individual sensing element is adhesively secured to the sensor holder or fixture and is ready for use.

In more detail now, the present methods, and composites, sensing elements, and materials employed therein are as follows.

A sensing composition precursor is formed or otherwise provided. Such precursor is useful to be applied, preferably as a continuous, more preferably as a substantially uniform continuous, coating on the continuous web and, while on the web, to be reacted or otherwise converted or transformed into the presently useful continuous sensing composition. The sensing composition, and preferably the sensing composition precursor, includes an effective amount of a sensing component which is responsive to, and provides signals indicative of, the analyte of interest. The sensing composition precursor is preferably such that the resulting sensing composition is permeable to the analyte of interest.

Although any suitable such sensing composition precursor may be employed, in a particularly useful embodiment the precursor comprises a sensing component and a polymer precursor, that is a precursor of a polymeric material which is part of the sensing composition.

The polymeric material of the sensing composition is permeable to the analyte, preferably gas, of interest in the medium being monitored, and is permeable or transparent to the wave lengths of light utilized when, as is preferred, optical signals are used in sensing the analyte. Further, if the sensing composition is to be used in sensing carbon dioxide, this polymeric material is preferably impermeable to ions and to liquid water. For example, if the sensing component is dissolved in a dispersed aqueous liquid and, as is preferred, the aqueous liquid contains a buffer, the concentration of the buffer ions is preferably maintained substantially constant so that the sensing composition provides consistent signals in response to the concentration of the analyte of interest, carbon dioxide, in the medium.

Any suitable polymeric material may be employed in the present gas sensing compositions provided that the polymeric material has no substantial detrimental effect on the functioning of the present system or on the medium being monitored. Because of substantial gas and light permeability and aqueous impermeability properties, silicone-based polymeric materials are preferred. More preferably, cross-linked silicone-based polymeric materials are employed. When the analyte of interest is carbon dioxide or oxygen, the polymeric material is preferably cross-linked polydimethyl siloxane or copolymers of polydimethyl siloxane.

The precursor of the polymeric material, the polymer precursor, may be selected from one or more monomers, pre-polymers, and mixtures thereof. In one embodiment, the polymer precursor is a precursor of a vinyl/hydride addition cure polysiloxane polymer. A particularly useful polymer precursor, e.g., when carbon dioxide or oxygen is the analyte of interest, is vinyl terminated dimethyl siloxane. If the polymeric material is to be cross-linked, a cross-linking agent is included with the polymer precursor. Such cross-linking agents are preferably compounds which include at least three functional groups per molecule capable of reacting with the polymer precursor and/or a partially polymerized intermediate to form cross links, e.g., between polymer chains, in the polymeric material. A particularly useful cross-linking agent is methylhydro-dimethylsiloxane copolymer especially when the polymer precursor includes vinyl terminated dimethylsiloxane.

One or more catalysts may be used to promote the formation, by polymerization, of the polymeric material. One such catalyst is platinum. The sensing composition precursor, including a catalyst component, may be exposed or subjected to elevated temperature sufficient to facilitate the catalyst component in promoting polymerization. Such elevated temperatures are greater than ambient temperature (22° C.) and preferably are in the range of about 40° C. to about 100° C. or more. The amount of catalyst component used should be sufficient to promote the desired degree of polymerization. Of course, the catalyst component should have no substantial detrimental effect on the functioning of the present system or on the medium being monitored. As used herein, the terms "polymerization" and "polymerizing" relate to one or more chemical reactions, including cross-linking, by which a polymer or polymeric material is formed.

In a useful embodiment, the catalyst component is chosen so as to be activated (for example, to promote polymerization of the polymer precursor), such as photo activated, upon being exposed to one or more factors, such as to light energy, preferably selected from visible light energy and ultraviolet light energy, and/or elevated temperatures, as defined herein, and the like. One substantial advantage of such a "factor" activated catalyst is that the polymer precursor, including the catalyst, can be prepared and maintained as such for relatively long periods of time by avoiding exposing the precursor to the "activating factor". Thus, one important process variable, that is the time when the polymer precursor is polymerized, in producing the present sensors is controlled so that the need to follow a tight production schedule because of the spontaneous polymerization of the polymer precursor is advantageously reduced. When it is desired to polymerize the polymer precursor, the precursor is simply exposed to the "activating factor". A particularly useful class of "factor activated" catalysts are those which are activated by light energy and, after being activated by sufficient light energy, are effective to partially polymerize the polymer precursor and are also effective upon being exposed to elevated temperatures to promote further polymerization of the partially polymerized polymer precursor.

Any suitable "factor" activated catalyst may be employed in the present invention, provided such catalyst has no substantial detrimental effect on the present system or on the medium being monitored. Photo-activated hydrosilylation catalyst systems are particularly useful. Certain platinum group metal-containing materials are very effective "factor activated" catalysts for use in the present invention. A number of such catalyst components are disclosed in Drahnak U.S. Pat. Nos. 4,510,094 and 4,530,879 and 4,600,484, and in Boardman et al U.S. Pat. No. 4,916,169, each of which is incorporated in its entirety herein by reference. Specific examples include cyclopentadienyl trimethyl platinum, derivatives thereof and mixtures thereof, particularly those which, after being activated by visible light energy or ultraviolet light energy, provide additional effective catalytic activity at elevated temperatures. The use of a combination of light energy and elevated temperatures to facilitate polymerization of the polymer precursor allows the polymerization to occur more rapidly and/or more completely relative to systems in which only light energy is employed.

Alternately, the silicone-based polymeric material can be formed through condensation polymerization reactions with silanol terminated silicones being cross-linked with alkoxyl silanes using catalysts, such as tin derivatives.

Fillers can be, and preferably are, included in the present gas sensing compositions which include dispersed aqueous liquid. Such fillers act to enhance the stability of the dispersed aqueous liquid in the sensing composition and the strength of the sensing composition. Any suitable filler may be used provided it has no substantial detrimental effect on the functioning of the present system or on the medium being monitored. In one embodiment, the filler has a hydrophobic nature. Such fillers are preferably present in an amount in the range of about 1% to about 20% by weight, based on the amount of polymeric material present in the gas sensing composition. A particularly useful filler is hydrophobic fumed silica, e.g., in the form of fine particles.

The sensing component or components chosen for use are those effective to provide a signal which varies in response to variations in the analytes, for example, concentrations of the gas, of interest in the medium being monitored. The sensing component is preferably an optical indicator, such as fluorescence indicators and absorbance indicators, in particular fluorescence indicators.

In sensing carbon dioxide concentrations, examples of absorbance indicators that can be used include chlorophenyl red, bromo cresol purple, nitrophenol, bromo thymol blue, penachlorome, pheno red and the like. Useful fluorescence indicators for carbon dioxide include hydroxypyrene 3,6,8-trisulfonic acid, herein referred to as HPTS or hydroxypyrene trisulfonic acid, derivatives, e.g., salts, of HPTS, beta-methylumbelliferone, fluorescein and the like. The more preferred sensing component, particularly for sensing the concentration of carbon dioxide in blood, is selected from HPTS, derivatives of HPTS and mixtures thereof. The alkali and alkaline earth metal salts of HPTS are useful HPTS derivatives.

In oxygen sensing concentrations, examples of fluorescence indicators include one or more polynuclear aromatic compounds, derivatives of polynuclear aromatic compounds and the like. Examples of such polynuclear aromatic compounds include decacyclene, benzo-ghi-perylene and coronene. The oxygen indicators may include a mixture of tertiary butyl derivatives of such polynuclear aromatic compounds. Such indicators are more fully described in Yafuso, et al U.S. Pat. No. 4,849,172 which is incorporated in its entirety herein by reference.

The oxygen indicators may be covalently bonded to the polymeric materials or matrix materials included in the sensing composition, for example, so as not to be leachable into the medium being monitored. Such covalent bonding is preferably accomplished by providing an oxygen indicator component including a reactable group which reacts with a reactable group, preferably a different reactable group, present in one of the components of the precursor of the polymeric matrix material. Thus, during the formation of the polymeric matrix material, the above-noted reactable groups also react to covalently bond the oxygen indicator to the matrix material. Particularly useful oxygen indicator components include the above-noted polynuclear aromatic compounds derivatized to include a reactable group, such as a reactable group with functional carbon-carbon unsaturation. The vinyl derivatives of such compounds provide excellent results.

The amount of sensing component used is such as to provide a sufficiently strong signal so that the analyte of interest can be reliably and accurately determined.

The present sensing composition precursors and sensing compositions which include an aqueous liquid, such as those useful in sensing carbon dioxide, preferably also include an effective amount of at least one dispersing agent. Such agents act to facilitate maintaining the aqueous liquid dispersed in the sensing composition precursor prior to forming the polymeric material.

Any suitable dispersing agent may be used provided that such agent has no substantial detrimental effect on the functioning of the present system or on the medium being monitored. Examples of dispersing agents include water-soluble dextran, polyvinyl alcohol, poly(ethylene oxide), polyvinylpyrrolidone, hydroxyalkyl celluloses, and the like materials. The amount of dispersing agent utilized may vary depending, for example, on the specific dispersing agent, polymer precursor and filler being employed. In one embodiment, the amount of dispersing agent present is in the range of about 1% to about 40% by weight of the total aqueous liquid employed.

The precursor for the carbon dioxide sensing composition may be prepared as follows. The carbon dioxide sensing component is dissolved in a quantity of liquid water to form an aqueous liquid. If desired, a buffer and/or dispersing agent can also be dissolved in this aqueous liquid. The desired amount of polymer precursor, and, if desired, a filler component and polymerization catalyst, is (are) mixed with the aqueous liquid. One or more cross-linking agents may or may not be present at this point.

The resulting mixture is subjected to strong agitation, for example, in a mechanical homogenizer, to disperse the aqueous liquid and form dispersed mixture. After this agitation, the dispersed mixture containing dispersed aqueous liquid can be stored for a period of time, e.g. on the order of about 1 hour to about 24 hours or more, ready for use.

A cross-linking agent or agents, if any, and a polymerization catalyst, if not already present, are added to the dispersed mixture. These are gently stirred into the dispersed mixture to form the sensing composition precursor.

After the sensing composition precursor has been prepared and degassed, a quantity of it is placed, preferably continuously placed, on one side of a continuous web. In one embodiment, the continuous web is transparent and/or is substantially impermeable to the analyte to be sensed. This precursor is preferably present on the continuous web as a continuous coating or sheet of substantially uniform thickness and composition. As noted previously, placing the precursor on the web continuously provides substantial sensing element manufacturing benefits and, ultimately, produces high quality sensing elements reliably and cost effectively. In one useful embodiment, the continuous placing of the precursor on the web is accomplished by continuously passing or moving the continuous web, preferably at a constant speed, in proximity to the stationary outlet of a coating apparatus which provides the precursor to the web through the outlet.

Other coating methods effective to place, preferably continuously place, the sensing composition precursor on the continuous web may be employed. Many coating methods are conventional and well known in the coating art. Examples of such methods include roll coating; brush coating; knife coating, such as coating using a floating knife, air knife coating, knife-over-blanket coating and knife-over-roll coating; blade coating; rod coating; dip coating; squeeze roll coating; levelon coating; kiss coating; gravure coating; reverse roll coating; curtain coating; extrusion coating; slot-orifice coating; calender coating; precast coating; cast coating; spray coating; atomization; vacuum coating; sputtering and the like. Since the sensing composition precursor is preferably continuously placed or coated on the continuous web, it is preferred that the coating method chosen be such that the web is in motion as it is being coated with precursor, more preferably from a stationary source of precursor. This "moving web" type of process provides easy and effective control of the coating operation so that substantially uniform coating of relatively long lengths of, for example, lengths of at least about 2 feet or at least about 5 feet to about 20 feet or about 50 feet or more, continuous web is achieved.

The continuous web can be conveniently located on or in the form of a roll prior to being passed for coating. After the continuous sensing composition is formed from the precursor coating, the sensing composition-containing web can be placed on a roll or maintained in the form of a roll in anticipation of the next processing step. In addition, other intermediate products described herein can be placed on rolls or maintained as rolls of material in between processing steps.

The precursor for the oxygen sensing composition may be prepared in a somewhat analogous manner to the carbon dioxide sensing composition precursor except that no aqueous liquid is used and an organic solvent is used to combine the sensing component into the polymer precursor. In one embodiment, the continuous web (and the web layer of the individual sensing elements) is transparent, and preferably is at least relatively (for example, relative to the sensing composition) analyte or gas impermeable. Thus, the continuous web and web layer are made of a material which allows the signal or signals, preferably the optical signal or signals, from the sensing component to pass through. Particularly useful materials of construction for this continuous web and web layer include polymeric materials, such as polyesters, polycarbonates, polysulfones including, but not limited to, polyethersulfones and polyphenylsulfones, polyvinylidine fluoride, polymethyl pentenes and the like. In an alternate embodiment, the continuous web comprises a continuous opaque film, as described elsewhere herein. In this embodiment, the continuous web (and the web layer of the individual sensing elements) has the structure of and functions as a continuous opaque film (and the opaque layer of the individual sensing elements) as described elsewhere herein. In this embodiment, the individual sensing elements are secured to a sensor holder or fixture so that the opaque layer provides a degree of optical isolation for the sensing element while, at the same time, allowing signals indicative of the concentration of an analyte in a medium to be effectively provided by the sensing composition layer.

A further embodiment involves the production of sensing elements each of which includes no portion of the continuous web, that is includes no web layer. For example, once the sensing composition-containing web is formed, the continuous web can be removed from this sensing composition-containing web. Such removal may involve physically stripping the web from the continuous sensing composition, exposing the sensing composition-containing web to a selective solvent to dissolve the continuous web and/or one or more other web removing steps. Care should be exercised to avoid damaging the sensing composition in removing the web. For example, it may be advantageous to employ a water soluble web material, such as polyvinyl alcohol or the like, so that water can be used to remove the web without substantially detrimentally affecting the continuous sensing composition.

Each of the individual sensing elements preferably includes opposing end surfaces, spaced apart by the thickness of the element, which are substantially mutually parallel. Each sensing element is preferably shaped to at least partially fit into a cavity or indent of a sensor holder or cassette, as described herein, preferably with one end surface facing the wall opposite the open end of the sensor holder cavity or indent. Each of the individual sensing elements produced in accordance with the present invention can, and preferably do, have the configuration of a right circular cylinder. In one embodiment, the web layer has a thickness in the range of about 0.0025 cm to about 0.254 cm, and preferably a diameter in the range of about 0.127 cm to about 1.27 cm. The individual sensing elements preferably have similar diameters.

If the sensing elements are to include a web layer, the continuous web is preferably treated or coated to enhance or increase the adhesion between the web and the precursor (and resulting sensing composition) relative to the level of adhesion between an identical web and precursor (and resulting sensing composition) without the web being so treated or coated. The treatment or coating should be chosen so as to have no substantial detrimental effect on the present system or on the medium being monitored. The continuous web can be exposed to one or more plasmas and/or corona discharges and/or other surface modification techniques to obtain this enhanced adhesion ability.

In a particularly useful embodiment, the continuous web is coated with an adhesion enhancing component in an amount effective to increase the adhesion between the web and the precursor (and resulting sensing composition) relative to the level of adhesion between an identical web and precursor (and resulting sensing composition) without the adhesion enhancing component. Examples of useful adhesion enhancing components include primer components, coupling agents and the like, many of which are commercially available. Examples include primer components comprising mixtures of inorganic oxide particles and ambifunctional silanes, such as those described in Van Ooij et al U.S. Pat. No. 5,204,219, which is incorporated in its entirety herein by reference. A very useful adhesion enhancement component for use in the present invention is obtained by coating the web with an aqueous mixture comprising water, silica particles and aminopropyltriethoxysilane.

Alternately, webs can be obtained from materials which have been pretreated or precoated to provide enhanced adhesion, such as, for example, the product sold by Hoechst Celanese under the trademark Hostaphane SA.

The sensing composition precursor located on the continuous web is converted or otherwise transformed into the continuous sensing composition. When, as is preferred, this sensing composition precursor includes a polymer precursor, this forming step comprises polymerizing, including cross-linking, the polymer precursor. This sensing composition forming step is preferably conducted at conditions effective to form the sensing composition without substantially detrimentally affecting the web or other components of the present system. Visible light energy or ultraviolet light energy and/or temperature, preferably in the range of about ambient temperature (22° C.) or elevated temperature, as described herein, are often very effective in curing the preferred silicone polymer precursor to form a cross-linked silicone polymer-containing sensing composition.

After the sensing composition precursor has been processed to form the continuous sensing composition, a continuous film of opaque material is preferably placed, for example, applied or formed, on the continuous sensing composition in such a manner that the sensing composition is located between the continuous web and the opaque film. This opaque film comprises the material from which the opaque layer of the present individual sensing elements is derived. The opaque film may be in the form of a porous membrane provided it has sufficient opacity and other properties to function as described herein as an opaque film.

The opaque film and opaque layer are made of a material which is analyte, preferably gas, permeable. This opaque layer acts to provide a substantial degree of optical isolation for the sensing composition layer. This optical isolation facilitates the providing of a substantially focused or directed signal from the sensing component to be transmitted for analysis, as described herein. Ultimately, such optical isolation often results in increased accuracy and reliability of the concentration determinations obtained using the present sensing elements. The opaque layer should be freely permeable to the analyte of interest in the medium being monitored. This opaque layer analyte permeability allows the analyte of interest from the medium to contact the sensing composition and interact with the sensing component. The opaque layer is preferably made from a polymer combined with an opaque agent.

Any suitable polymer may be included in the presently useful opaque layer, provided that the polymer has no substantial detrimental effect on the functioning of the present system or on the medium being monitored. The polymer chosen preferably provides a relatively thin film with sufficient structural integrity and durability to be useful in the present methods and sensing elements. In one embodiment, the opaque film includes a fluorine-containing polymer, preferably a polymer selected from polyfluorohydrocarbons, polyfluorocarbons and mixtures thereof, and especially, polytetrafluoroethylene.

Although a pre-formed opaque film can be applied to the continuous sensing composition, in one particularly useful embodiment the opaque film is formed in situ, that is on the sensing composition. Thus, a mixture containing a precursor component of the polymer to be included in the opaque film and an opaque agent is applied to or placed (coated) on, preferably continuously placed on, the sensing composition. This applied mixture is polymerized, for example, cured, to form the opaque film. This method of forming the opaque film provides substantial advantages, for example, providing an opaque film having a substantially uniform thickness which is strongly secured to the sensing composition. Employing continuous processing to apply the mixture to the sensing composition, as described herein, provides additional benefits many of which are similar or analogous to the benefits achieved by continuously placing the sensing composition precursor on the continuous web.

The chemical make-up of the polymer included in the opaque film may be the same as or different from that of the polymeric matrix material of the sensing composition. In a very useful embodiment, the polymer included in the opaque film is a silicone-based polymer, preferably such a polymer with a similar, or even substantially the same, chemical make-up as the silicone-based polymeric matrix materials included in the sensing compositions. The use of silicone-based polymeric materials in the opaque film results in sensing elements and sensors which advantageously have more rapid response times. In one embodiment, the opaque film includes a vinyl/hydride addition cure polysiloxane polymer. A specific example of a useful polymer for inclusion in the opaque film is a polymer derived from vinyl terminated dimethyl siloxane, such as that described previously with regard to the polymeric matrix material of the sensing compositions. Opaque films including such polymers can be formed in situ on the sensing composition in substantially the same manner as described previously with regard to the formation of the sensing composition except that an effective amount of a suitable opaque agent is used in place of the sensing component. One exception is that photo-activated catalysts are generally not used in producing the opaque film.

Any suitable opaque agent may be used provided that such agent or agents function to provide the desired degree of optical isolation and have no substantial detrimental effect on the functioning of the present system or on the medium being monitored. Among the opaque agents useful in the present invention are carbon black, other carbon based opaque agents, ferric oxide, $T_iO_2$, $BaSO_4$, metallic phthalocyanines and the like. Such opaque agents are preferably substantially uniformly dispersed in the opaque layer in an amount effective to provide the desired degree of opacity, e.g., to provide the desired optical isolation. A particularly useful opaque agent is carbon black.

Preferably, the opaque film is substantially thinner than the typical continuous web, for example, to facilitate analyte permeability. More preferably, the thickness of the opaque film is in the range of about 1% to about 20% of the thickness of the typical continuous web. In one embodiment, the opaque film has a thickness between 0.0001 cm to 0.005 cm, more preferably between 0.0003 cm to 0.0025 cm, most preferably between 0.0005 cm to 0.0015 cm.

Like the web, the continuous opaque film preferably includes opposing end surfaces which are substantially mutually parallel. In one particularly useful embodiment, one of the end surfaces of the opaque film is structured to bond or adhere to the continuous sensing composition. This feature advantageously increases the integrity of the composite structures and individual sensing elements in accordance with the present invention. Such end surface in contact with the continuous sensing composition may inherently be structured to provide this enhanced opaque film/sensing composition bond strength, or it (and/or the sensing composition) can be treated, for example, by exposure to plasma and/or corona discharge and/or by being coated with a primer agent and/or coupling component and/or by being subjected to other surface modification techniques, so as to provide this enhanced bond strength. Pressure, such a laminating pressure, can be applied to the transparent web/sensing composition/opaque film composite to obtain enhanced bond strength between the components of the composite.

Once this continuous web/sensing composition/opaque film composite structure is formed, random samples of the composite can be removed and tested or screened, using conventional techniques, to determine if the composite structure meets the product specifications for sensing elements in the desired application. If such testing or screening determines that the composite structure is not within product specifications, it can be discarded and the process started again. However, if the results of the random testing or screening are positive, that is that the composite structure does meet product specifications, no further testing may be needed prior to using individual sensing elements derived from this composite structure in a sensing application. If this composite structure is rolled up, it may be desirable to have a non-adhesive layer or sheet between the layers of composite on the roll. This non-adhesive sheet prevents the composite layers on the roll from sticking together.

Assuming that a composite structure meeting product specifications has been produced, the structure is then processed, for example, using a punch, a "cookie cutter-type" device or the like cutting device to form individual sensing elements, which are then available for being secured to a sensor holder or fixture for use. For example, the individual sensing elements can be placed at least partially in an open ended cavity in a sensor cassette. The sensing element is secured, for example, by adhesive, to the sensor holder. Any suitable, preferably transparent, cure-in-place adhesive composition may be employed, provided that such compositions have no substantial detrimental effect on the present system or on the medium being monitored. Examples include silicone-based adhesives, two part urethane adhesives, epoxy adhesives and the like. As previously mentioned, the sensing composition itself can also perform the function of the adhesive member and stick or adhere to the sensor holder. Alternately, the sensing element can be secured to the sensor holder or fixture mechanically, such as through the use of clamps or other mechanical securement assemblies, or can be press fitted in place on the sensor holder or fixture. Other approaches may be employed to secure the sensing element to the sensor holder or fixture.

The sensing element is situated relative to the sensor holder so that the web layer is preferably located relatively near to and facing the sensor holder, for example, the bottom of the open ended cavity of the sensor cassette, and the opaque layer is exposed to the medium being monitored. Sensing elements which include no separate web layer and/or no opaque layer may be produced and utilized in accordance with the present invention.

The sensor holder is preferably placed in proximity to an excitation assembly positioned and adapted to provide an excitation signal to the sensing element. A detector assembly is positioned and adapted to detect an emitted signal from the sensing element, which is capable of providing the emitted signal in response to being exposed to the excitation signal. A processor assembly is positioned and adapted to analyze the emitted signal (or a signal corresponding to the emitted signal) in determining the concentration of the analyte of interest in the system being monitored.

Once the above-noted continuous web/sensing composition/opaque film composite structure has been found to meet product specifications, it can alternately be processed as follows.

A continuous film of adhesive composition, which is chosen to have no substantial detrimental effect on the present system or on the medium being monitored, is applied to the side of the continuous web opposite the side in contact with the sensing composition. This adhesive film preferably comprises a pressure sensitive adhesive composition. Specific examples of adhesive compositions useful in the present invention include the pressure sensitive adhesive (PSA) compositions sold by General Electric under the trademarks PSA 518 and PSA 590. The amount of adhesive film employed is sufficient so that the final individual sensing elements produced include an adhesive composition layer derived therefrom effective to adhesively secure the individual sensing elements to the sensor holder or fixture.

In a particularly useful embodiment, the adhesive composition is applied to a continuous, preferably non-adhesive, release liner and then, the continuous web is coupled or joined to the adhesive composition. The release liner preferably does not form a strong adhesive bond to the adhesive composition employed. Examples of materials from which the release liner can be made include various polymeric materials, such as various polyesters, for example, a polyester coated with perfluoro polyether sold by Minnesota Mining and Manufacturing Company under the trademark Scotch Pack 1022 and a fluoro silicone polyester sold by H.P. Smith under the trademark FL 2000, and the like.

Once this release liner/adhesive composition/web/sensing composition/opaque film composite structure has been formed, it is processed to convert the structure into a plurality of individual sensing elements which are still carried by the release liner. This convening step, which is preferably accomplished with "cookie-cutter-type" cutting assemblies, other cutting equipment or the like equipment, cuts through each of the individual layers of the structure except for the release liner, which remains substantially intact. Thus, each of the individual sensing elements includes an opaque layer, a sensing composition layer, a web layer and an adhesive layer.

After this conversion, non-sensing element material or weed, that is material which is not included in any one of the individual sensing elements, is removed from the release liner. This non-sensing element material may be used to test and screen to determine if the individual sensing elements carded by the release liner are within product specifications. This non-sensing element material is discarded. In addition, a selected and representative sampling of the sensing elements on the release liner may be tested and screened to determine if the sensing elements carried by the release liner are within product specifications.

Once it has been determined that such sensing elements are within product specifications, they can be individually removed from the release liner and secured to a sensor holder or fixture for use. For example, such an individual sensing element can be placed in an open ended cavity of a sensor cassette such that the adhesive layer is in contact with the bottom of the open ended cavity. Simply by pressing the sensing element into the cavity, the preferred pressure sensitive adhesive composition is activated to securely adhere the sensing element to the sensor holder or cassette. The sensing element is now ready for use, preferably in combination with an excitation assembly, a detector assembly, and a processor assembly, as described elsewhere herein.

When sensing carbon dioxide, a particularly useful sensing composition comprises a two phase system comprised of a pH indicator containing an aqueous phase encapsulated in a non-polar, $CO_2$ permeable barrier material. Unfortunately a characteristic feature of these types of sensors is reversible "$CO_2$ conditioning drift", a response instability accentuated by large changes in $CO_2$ partial pressure. We have discovered an optical fluorescence based sensor (e.g., for measuring $CO_2$ concentration in a medium such as blood) with improved drift stability. We have discovered that adventitious pH-titratable partitioning species other than the analyte of interest can reversibly migrate between the indicator and barrier phases as a function of pH, and therefore as a function of $CO_2$ partial pressure. We have also discovered that these species can also irreversibly migrate (or "leach") from the sensor to the medium. The migration of the partitioning species generates a pH response which can substantially affect the analyte concentration dependent signal. By careful choice and/or purification of sensor materials and components, we have minimized the presence of these adventitious species and developed a substantially drift-free sensor formulation. Alternatively, by proper choice of buffer composition and indicator pKa, we have discovered compositions which minimize the $CO_2$ dependent migration of adventitious species, further stabilizing these sensors.

We have made the unexpected discovery that one cause of the drift instability (commonly referred to as "analyte conditioning drift" or more specifically as "$CO_2$ conditioning drift") is actually a pH hysteresis phenomenon resulting from the presence of pH-titratable materials (hereinafter referred to as "partitioning species") which migrate in and out of the aqueous indicator phase as a function of internal pH, and therefore as a function of $CO_2$ partial pressure. While ionized species are essentially insoluble in non-polar barrier materials such as silicone, the neutral form of organic acids or bases can be very soluble in both the aqueous and silicone phases. For example, if an air equilibrated sensor comprising a sodium acetate impurity in the aqueous indicator phase is suddenly exposed to an elevated $CO_2$ level, such that the internal compartment pH drops from pH 9 to pH 7, a sudden 100 fold increase in acetic acid concentration occurs creating a thermodynamic driving force for slow migration of charge neutral acid into the silicone. Acid depletion from the aqueous indicator phase then induces additional $CO_2$ uptake and further protonation of acetate ions. This replacement of sodium acetate by sodium bicarbonate changes the $pH/pCO_2$ relationship for the aqueous indicator phase, resulting in a slow rise in pH in opposition to the initially imposed pH drop. The migration or "partitioning" process continues until the equilibrium partitioning ratio for acetic acid is reestablished between the aqueous indicator phase and the silicone. Upon returning to the air equilibrated baseline the process is reversed. Although not recognizing the cause of the $CO_2$ drift problem, it has been a customary practice in the sensor field to package continuous blood gas monitoring sensors in a "$CO_2$ conditioned state" (i.e., at elevated $CO_2$ levels) thereby somewhat reducing excessive drift upon initial exposure to physiological $CO_2$ levels. With our new formulation, this practice should no longer be required.

A corresponding hysteresis process is operative for organic bases such as amines, since they can also migrate from the silicone phase into the aqueous indicator phase when the $CO_2$ level is elevated. For example, if an air equilibrated sensor comprising an amine impurity in the silicone phase is suddenly exposed to an elevated $CO_2$ level, such that the internal compartment pH drops from pH 9 to pH 7, a sudden 100 fold increase in ammonium ion concentration occurs creating a thermodynamic driving force for slow migration of charge neutral amine from the silicone into the aqueous phase. Amine uptake to the aqueous indicator phase then induces additional $CO_2$ uptake and further protonation of amine. This accumulation of ammonium ions changes the $pH/pCO_2$ relationship for the aqueous indicator phase, resulting in a slow rise in pH in opposition to the initially imposed pH drop. The migration or "partitioning" process continues until the equilibrium partitioning ratio for amine is reestablished. Upon returning to the air equilibrated baseline the process is reversed. Notably, the effect on the sensor response is identical for both acetate depletion and amine uptake; that is, when moved from an air equilibrated medium to a medium equilibrated at a higher $CO_2$ level, a negative mm drift will result in the presence of either type of species. This hysteresis process can also occur for the indicator dye itself if the dye exists in equilibrium with a partitionable charge neutral form.

Another cause of drift instability (referred to as "saline conditioning drift" or "saline drift") is actually a pH dependent phenomenon resulting from the presence of pH-titratable materials which migrate from the sensor to the medium as a function of external pH, and therefore as a function of $CO_2$ partial pressure. For example, if an air equilibrated sensor comprising an amine impurity in the silicone is suddenly exposed to an elevated $CO_2$ level, the pH of the external buffer drops from pH 9 to pH 7, creating a driving force for slow migration of charge neutral amine from the silicone into the external aqueous medium where it becomes protonated. This process impacts the amount of amine available for partitioning into the internal aqueous compartment. Notably, the effect on the sensor response is opposite to the previously discussed $CO_2$ conditioning drift. That is to say, the sensor exhibits a positive mm drift due to these migrating species.

With this new understanding, we have developed new $CO_2$ sensor formulations which contain less than a critical amount of titratable partitioning species, and exhibit substantially drift free response. As used herein the terms "drift free" or "substantially drift free" mean that the sensor provides a signal which drifts less than 12% (i.e., <5.5 mm) over a three hour period when moved from a medium equilibrated with a gas having a $pCO_2$ of 0.25 mm to a medium equilibrated with a gas having a $pCO_2$ of 45.6 mm as herein described (see Example 1 and FIG. 3b for details of this calculation). More preferably, the sensor provides a signal which drifts less than 6% when moved from a medium equilibrated with a gas having a $pCO_2$ of 0.25 mm (i.e., air equilibrated) to a medium equilibrated with a gas having a $pCO_2$ of 45.6 mm. Most preferably, the sensor provides a signal which drifts less than 3% when moved from a medium equilibrated with a gas having a $pCO_2$ of 0.25 mm to a medium equilibrated with a gas having a $pCO_2$ of 45.6 mm. This advance offers several practical advantages.

In one embodiment, the sensor is maintained in an air-equilibrated buffer condition, except during temporal physiological $CO_2$ sampling. For example, certain commercial ex-vivo sensing systems contain a sensing element (e.g., a sensor composition housed in a cassette which is attached to an optical fiber or which alternatively contains an excitation light source) in the a-line circuit of arterially catheterized patients. Blood gas levels are monitored temporally (e.g., "on demand" by the health care provider or automatically by means of a programmed pump or motor) by drawing blood up the saline drip line into the sensor cassette, and then allowing the blood to return to the patient. The present invention, when used in such a configuration, should remove earlier limitations on the frequency and duration of physiological $CO_2$ sampling that can be achieved without incurring or inducing drift.

Sensors of the present invention are easily calibrated and may reside in the calibration medium before, during and after calibration without the special precautions commonly employed to limit "$CO_2$ conditioning drift" or "saline drift".

In general, the magnitude of drift exhibited by traditional sensors is proportional with the buffering capacity of the aqueous indicator compartment. Sensors of the present invention, preferably being substantially free of partitioning species, enjoy the advantage of being far less susceptible to drift even when the buffering capacity of the aqueous indicator phase is decreased. This enables design of sensors with a faster response time, without introducing a prohibitive rate and/or amount of drift. In addition, the gas sensors of the invention are stable (i.e., drift free), reproducible and tolerant of production variables without detracting from the inherent properties of the gas sensors. Alternatively, one can reduce the drift exhibited by sensors that contain small amounts of partitioning species by employing higher buffer concentrations as herein described. Finally, one may combine a higher buffer concentration with a "clean" sensor chemistry and produce a drift free sensor which is less susceptible to externally induced drift such as might be caused by exposure of the sensor to a medium which contains a partitioning species.

This can be advantageously accomplished in a gas sensor which comprises an aqueous first phase including a dye and a hydrophobic second phase, and which is substantially free of partitioning impurities which can migrate from one phase to the other in response to a change in pH in the first phase and which substantially affect the concentration dependent signal. In a preferred embodiment, the first phase comprises an aqueous buffered solvent and a dye and the second phase comprises a cross-linked polymeric material which is gas permeable, light permeable and essentially aqueous impermeable.

In a presently preferred embodiment, the first and second phases are formed into a permanent "emulsoid" of suspended or dispersed micro-compartments of the aqueous first phase in the cross-linked polymeric second phase wherein the micro-compartments of the aqueous first phase are preferably smaller than 5 microns, and more preferably smaller than 2 microns.

In an illustrative embodiment of the invention, the dye is a pH sensitive dye, the aqueous buffer solvent is a physiological pH range buffer solution as for instance a bicarbonate ion or bicarbonate/phosphate ion based buffer solution. In this illustrative embodiment the polymeric material is a silicone material as for instance a siloxane material which is carbon dioxide permeable. More specifically the material is polydimethylsiloxane or polydimethylsiloxane copolymers. The dye in the illustrative embodiment is the trisodium salt of hydroxypyrene trisulfonic acid (HPTS").

In an illustrative embodiment of the process, the dye is present in the aqueous phase in a concentration of about 1 to about 15 millimolar and the buffer is present in the aqueous phase in a concentration of from about 1 to about 100 millimolar. More preferably, the dye and buffer are present in a concentration of from about 1 to about 10 and 1 to 50 millimolar, respectfully, and most preferably the dye and buffer are present in a concentration of from about 1 to 5 and 5 to 20 millimolar, respectfully.

A further advantageous process of preparing a gas sensor comprises dissolving a quantity of a dye in a quantity of aqueous buffer solution followed by vigorously mixing the buffer solution with a quantity of a polymeric precursor of a cross-linked polymeric material so as to form an emulsion (or suspension) of the buffer solution and the polymeric precursor. Then a quantity of a cross-linking agent and catalyst are added to the emulsion. The catalyzed emulsion is formed into a shape (e.g., coated into a sheet, as herein described, suitable for insertion into a sensor cassette) and cured to form a permanent emulsoid (which is substantially free of partitioning species which can migrate from one phase to the other in response to a change in pH in the buffer solution and which substantially affect the analyte concentration dependent signal) of micro-compartments of the dye containing aqueous buffer solution in the cross-linked polymeric material. The above process can be augmented by adding a quantity of an emulsification enhancement agent (e.g., a thickener or surfactant) to the solution of the dye in the buffer so as to form a mixture of the dye and the emulsification enhancement agent in the buffer and/or by adding a dispersing agent such as fumed silica to the hydrophobic phase.

The following non-limiting examples illustrate certain aspects of the present invention. Unless otherwise indicated, all parts and percentages are by weight.

EXAMPLES

Example 1

An aqueous solution is formed by dissolving 11.8 mg of hydroxypyrenetrisulfonate (trisodium salt), 375 mg of poly(ethylene oxide) having a molecular weight of 300,000, 31.4 mg of trisodium phosphate dodecahydrate, and 59.6 mg of sodium chloride in enough water to make 7.5 gm of solution.

A silicone mixture is prepared by combining 16.4 mg of cyclopentadienyl trimethyl platinum, (an ultraviolet light activated catalyst component), 0.49 gm of fumed silica, sold by Cabot under the trademark TS-530, and 15.91 gm of vinyl dimethyl end-capped poly(dimethyl siloxane) having a viscosity of 1000 centistokes and sold by NuSil Silicone Technology under the trademark PLY-7500. The aqueous solution is combined with the silicone mixture, and 1.1 gm of poly(dimethyl) (methylhydro)- siloxane, sold by NuSil Silicone Technology under the trademark XL-123, having a molecular weight of about 2100 and a silyl hydride group content of about 30%, is added. This combination is then processed with a Vertis Cyclone IQ homogenizer to form the sensing composition precursor.

A transparent, continuous polycarbonate web, having a thickness of about 0.0127 cm, is coated with an adhesion enhancement component derived from a mixture containing water, 1.25% by weight of colloidal silica particles, 0.11% by weight of aminopropyltriethoxysilane, 0.05% by weight ammonium hydroxide and 0.03% by weight of a surfactant sold by Rohm and Haas under the trademark Triton X-100.

Using a coating apparatus sold by Hirano under the trademark M-200, the sensing composition precursor is continuously coated on one side of the web. In this coating operation (and all other coating operations described herein using this coating apparatus), the web is moved, at a constant speed, in proximity to and under the coating apparatus which is stationary. This precursor coating has a substantially uniform thickness of about 0.0025 cm. The sensing composition precursor is cured by exposing the coating to about 70 mJ cm$^{-2}$ of ultraviolet (365 nm)light. The coating is further cured by exposure at about 90° C. for about 2 minutes to form the sensing composition.

An opaque film precursor is prepared by mixing 12 gm of a 12% by weight dispersion of carbon black, sold by Cabot under the trademark Regal 99R, in vinyl end-capped poly-(dimethyl)siloxane sold by NuSil Silicone Technology under the trademark PLY-7501, having a viscosity of 500 centistokes, with 26.6 mg of a platinum catalyst solution sold by NuSil Silicone Technology under the trademark Cat50, 6.5 mg of a polymerization inhibitor sold by Nusil Silicone Technology under the trademark XL119, and 0.6 gm of the poly(dimethyl)(methylhydro)siloxane noted above. Using the coating apparatus noted above, this opaque precursor is continuously coated on the sensing layer in a substantially uniform coating with a thickness of about 0.0013 cm. The opaque film precursor is cured by exposure at 70° C. for 2 minutes to form the opaque film.

Figure 2:
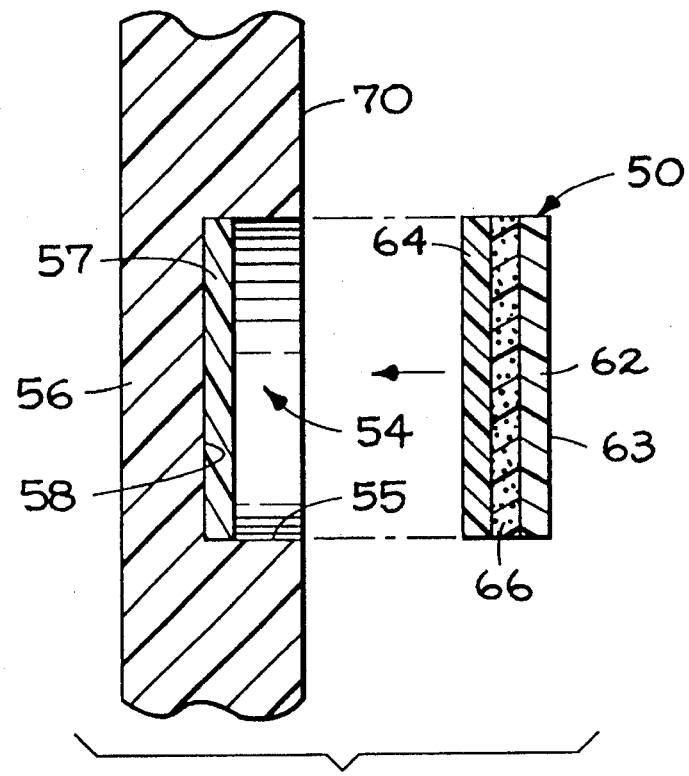
FIG. 2 is a cross sectional view showing an assembled sensing element being bonded to a sensor cassette.
Figure 3:
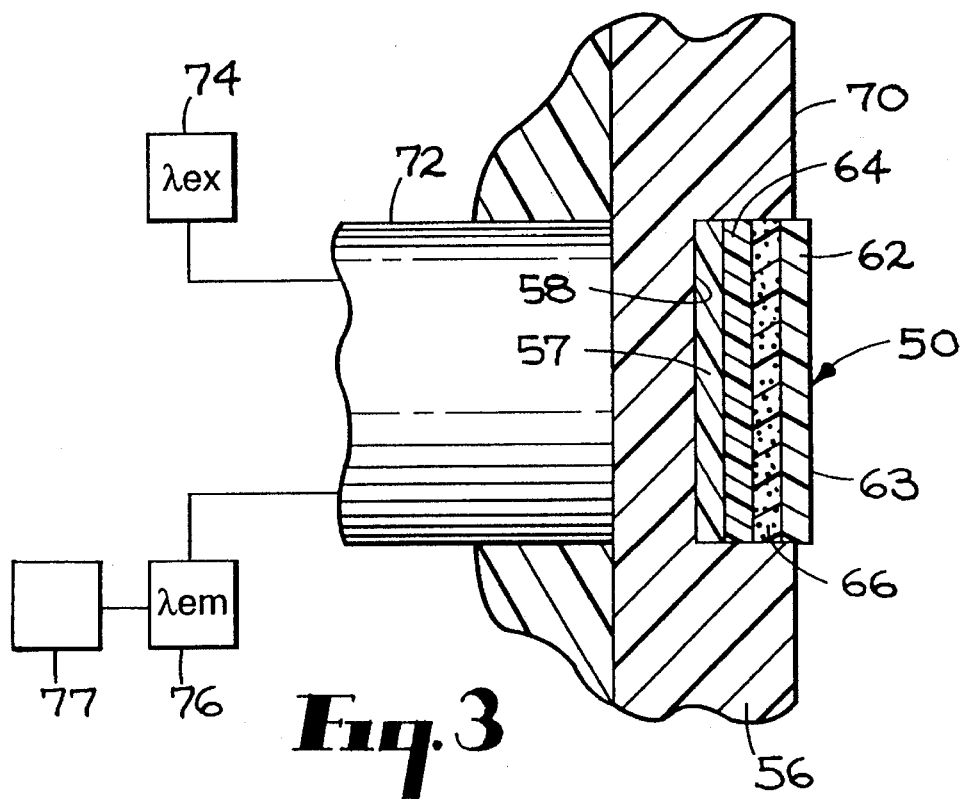
FIG. 3 is a schematic view showing a sensing element bonded to the sensor cassette for providing signals useful to sense the concentration of a gas in a medium.

Individual carbon dioxide sensing elements are cut from the continuous web/sensing composition/opaque film composite. Each sensing element includes a generally circularly shaped portion of the transparent web, a generally circularly shaped portion of an opaque film and a thin, generally circularly shaped layer of the sensing composition therebetween. Such an individual sensing element is illustrated in FIGS. 2 and 3.

Using conventional testing procedures, a small, representative sample of the individual carbon dioxide sensing elements is tested to determine if such elements meet product specifications, that is if such elements are effective for accurately and reliably sensing the concentration of carbon dioxide in human blood. These individual carbon dioxide sensing elements are found to be satisfactory based on this testing procedure.

Using a transparent silicone-based adhesive sold by Dow Corning under the trademark Dow Corning 3140, one of these carbon dioxide sensing elements is bonded into a right circular cylindrical open ended well, having a diameter of 0.317 cm and a depth of 0.025±0.0025 cm, formed in a polycarbonate cassette so that the transparent web layer is facing the bottom of the well. Prior to bonding the sensing elements to the cassette, the walls of the well are contacted with a priming agent, sold by Dow Chemical Company under the trademark Dow 1205, to promote adhesion between the sensing element and the polycarbonate cassette.

The thus produced carbon dioxide sensor is effective in determining the concentration of carbon dioxide in blood brought into contact with the opaque layer.

Example 2

Example 1 is repeated except that after the opaque film is formed the composite is processed as follows.

A release liner of a polyester film coated with perfluoro polyether and sold by Minnesota Mining and Manufacturing Company under the trademark Scotch Pack 1022 is coated on one side with a pressure sensitive adhesive composition sold by General Electric under the trademark PSA-518. This coated sheet is applied to the side of the transparent web opposite the sensing composition so that the adhesive is in contact with the transparent web.

Figure 4:
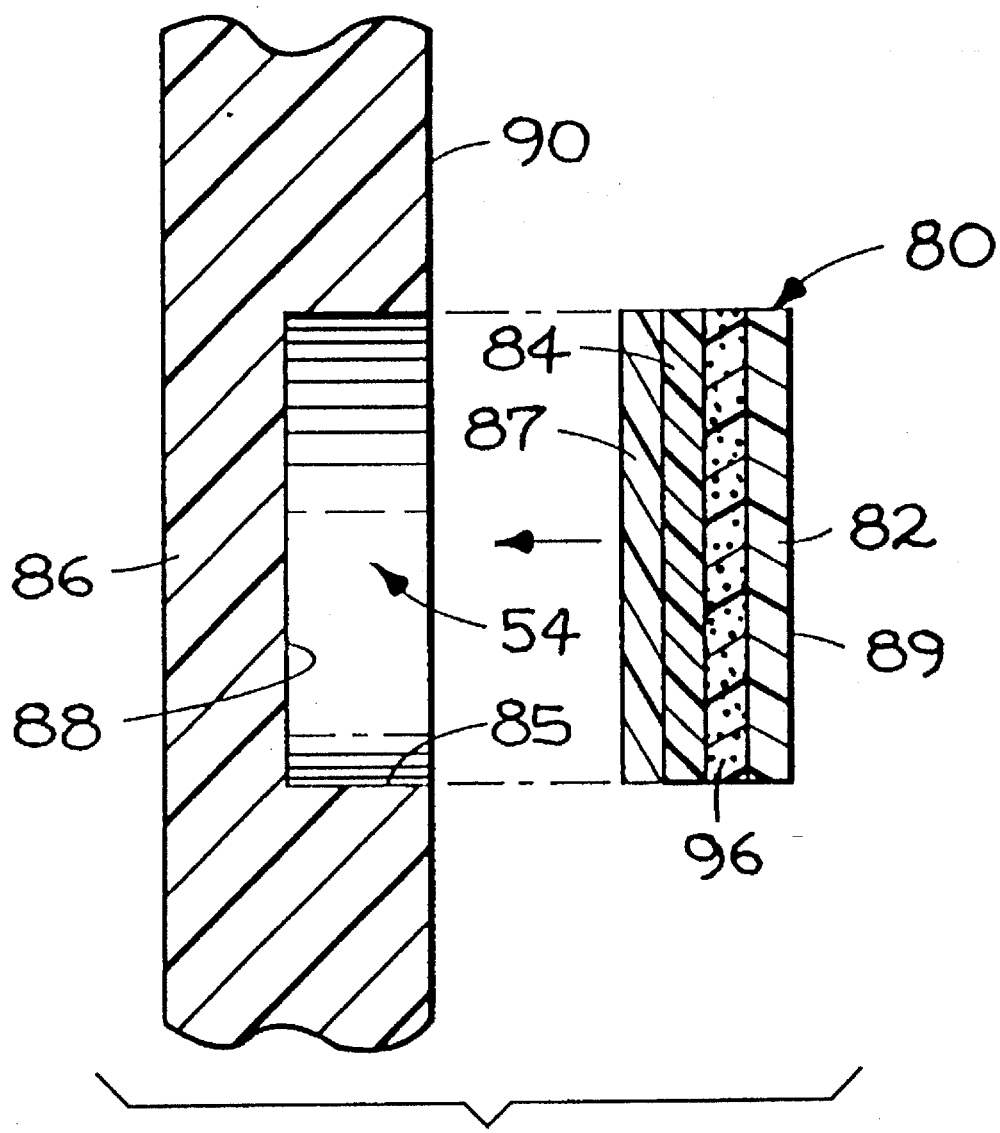
FIG. 4 is a cross sectional view showing an alternate embodiment of an assembled sensing element being bonded to a sensor cassette.

This formed composite is then subjected to a cutting operation such that generally fight circular cylindrical sensing elements are formed and remain located on the release liner which remains intact during this curing operation. Each of the sensing elements includes an opaque layer, a sensing composition layer, a transparent web layer and an adhesive composition layer. Such a sensing element is illustrated in FIG. 4.

After the cutting operation, the material which is located on the release liner which is not part of any sensing element is removed or weeded out from the release liner. This non-sensing element material is discarded.

A small, representative sample of the sensing elements located on the release liner are removed and tested, using conventional techniques, to determine whether or not the sensing elements on the release liner meet product specifications. Once it has been determined that these sensing elements are satisfactory, they can be used simply by removing them from the release liner and placing them in an open ended cavity of a sensor cassette so that the adhesive composition layer is in contact with the bottom of the sensor holder cavity. By pressing the sensing element into the cavity, the adhesive composition acts to securely adhere the sensing dement to the sensor cassette.

The thus produced carbon dioxide sensor is effective in determining the concentration of carbon dioxide in blood brought into contact with the opaque layer.

Example 3

A 0.457 gm portion of 4-vinylbenzo[g,h,i]perylene is mixed with 10.0 gm of poly(methylhydro)(dimethyl)-siloxane described in Example 1 and 300 ml toluene. A 100 microliter portion of a platinum catalyst solution sold by Huls America under the trademark PC 072 is added, and the solution is heated to reflux for 1 hour, then cooled to room temperature. A 8 gm portion of decolorizing charcoal is added. After stirring, the charcoal is removed by filtration. This step removes the platinum catalyst. The toluene is removed under vacuum, and the residue made up to 100 ml with hexane.

A 0.7 mg portion of cyclopentadienyl trimethylplatinum is dissolved in 7.0 gm of poly(dimethyl)siloxane having a viscosity of 500 centistokes. To this solution is added 1.9 ml of the hexane solution described above. The hexane is removed under vacuum to form the sensing layer precursor.

A transparent poly(ethylene terephthlate) web, having a thickness of 0.0127 cm, is coated with the adhesion enhancement component derived from the mixture described in Example 1. Using the coating apparatus identified in Example 1, this sensing composition precursor is continuously coated on one side of the web. This precursor coating has a substantially uniform thickness of about 0.0013 cm.

The sensing composition precursor is cured by exposing the coating to about 70 mJ cm$^{-2}$ of ultraviolet (365 nm) light. The coating is further cured by exposure at about 90° C. for about 2 minutes.

An opaque film precursor is prepared as described in Example 1. Using the coating apparatus identified in Example 1, this opaque precursor is continuously coated on the sensing layer in a substantially uniform coating, with a thickness of about 0.0008 cm. The opaque precursor is cured by exposure at 70° C. for 2 minutes.

Individual oxygen sensing elements are cut from the transparent web/sensing composition/opaque film composite. Each sensing element includes a generally circularly shaped portion of the transparent web, a generally circularly shaped portion of an opaque film and a thin, generally circularly shaped layer of the sensing composition therebetween.

Using conventional testing procedures, a small, representative sample of the individual oxygen sensing elements is tested to determine if such elements meet product specifications, that is if such elements are effective for accurately and reliably sensing the concentration of oxygen in human blood. These individual oxygen sensing elements are found to be satisfactory based on this testing procedure.

Using a transparent, room temperature vulcanizable silicone-based adhesive sold by General Electric under the trademark RTV 128, as sensing element, as noted above, is bonded into a right circular cylindrical open ended well, having a diameter of 0.3175 cm and a depth of 0.025±0.0025 cm, formed in a polycarbonate cassette so that the transparent web layer is facing the bottom of the wall. Prior to bonding the sensing element to the cassette, the walls of the well are contacted with a priming agent, sold by Dow Chemical Company under the trademark Dow 1205, to promote adhesion between the sensing element and the polycarbonate cassette.

The thus produced oxygen sensor is effective in determining the concentration of oxygen in blood brought into contact with the opaque layer.

Example 4

Example 2 is repeated except that the continuous web/sensing composition/opaque film composite of Example 3 is employed.

Sensors, including individual oxygen sensing elements, are produced and are effective in sensing the oxygen concentration of blood brought into contact with the opaque layer.

FIGS. 2 and 3 illustrate the use of a sensing element produced in Example 1 in determining carbon dioxide concentrations. A sensing element produced in Example 3 can be used in a substantially similar manner in determining oxygen concentrations.

As shown in FIGS. 2 and 3, this individual sensing element 50 is placed into well 54 of sensor holder 56 and bonded in place using a layer 57 of transparent, silicone-based adhesive. Well 54 is open at one end, includes a right circular cylindrical side wall 55 and a circular bottom end wall 58. The size of well 54 is such that the individual sensing element 50 and silicone-based adhesive layer 57 completely fill the well. Individual sensing element 50 is placed in well 54 so that the transparent web layer 64 faces the bottom end wall 58 of well 54. The opaque layer 62 includes an exposed surface 63 (FIG. 3) which is raised relative to the inner surface 70 of sensor holder 66. The opaque layer 62 substantially shields sensing composition layer 66 from direct contact with the medium, e.g., blood, to be monitored. Depending on the specific sensing application involved, the exposed surface of the opaque layer can be recessed relative to, or flush with, the inner surface of the sensor holder.

Referring now to FIG. 3, in use sensor holder 56, made of a transparent polycarbonate material, is placed in abutting relation to optical fiber 72. Optical fiber 72 provides excitation light of appropriate wavelength from light transmitting apparatus 74 to excite the sensing component in the sensing composition layer 66 to fluoresce and provide a signal characteristic of the concentration of carbon dioxide located in the medium in contact with the opaque film 62. This optical fiber 72 also transmits the signal which is emitted from the sensing component and passes such signal to a light detecting or receiving apparatus 76, from which a signal corresponding to this emitted signal is passed to a conventional electronic processor device 77 which processes or analyzes this emitted signal (the corresponding signal), e.g., as described in Lubbers et al U.S. Pat. No. Re. 31,879 and Heitzmann U.S. Pat. No. 4,557,900, in determining the concentration of carbon dioxide in this medium. The above-noted Heitzmann patent is incorporated by reference in its entirety herein.

Over a period of time the individual sensing element 50 provides consistent signals which are reliably correlated to the true and accurate concentration of carbon dioxide in the blood in contact with the opaque layer 62.

FIG. 4 illustrates the use of a sensing element produced in Example 2 in determining carbon dioxide concentrations. A sensing element produced in Example 4 can be used in a substantially similar manner in determining oxygen concentrations.

As shown in FIG. 4, this individual sensing element 80 is placed into well 54 of sensor holder 86 and is bonded in place using pressure sensitive adhesive layer 87, which is a component of the individual sensing element. Well 54 is open at one end, includes a right circular cylindrical side wall 85 and a circular bottom end wall 88. The size of the well 54 is such that the individual sensing element 80 completely fills the well. Individual gas sensing element 80 is placed in well 54 so that the transparent web layer 84 faces the bottom end wall 88 of well 54. The opaque layer 82 includes an exposed surface 89 which is raised relative to the inner surface 90 of sensor holder 86. The opaque layer 82 substantially shields sensing composition layer 86 from direct contact with the medium, e.g., blood, to be monitored. Depending on the specific sensing application involved, the exposed surface of the opaque layer can be recessed relative to, or flush with, the inner surface of the sensor holder.

Once the individual sensing element 80 is secured in well 54 of sensor holder 86, by manually pressing the sensing element into the well, it is employed in a manner analogous to the individual sensing element 50, as illustrated in FIG. 3.

Over a period of time, the sensing element 80 provides signals which are reliably correlated to the true and accurate concentration of carbon dioxide in the blood in contact with the opaque layer 82.

The present invention provides substantial benefits, for example, in terms of labor saving, cost saving and sensor performance. The present methods of mass producing sensing elements reduce the amount of labor and other resources needed to produce high quality sensors. The present methods provide for producing individual sensing elements which have substantially uniform characteristics, and avoid the variability inherently present in making individual sensing elements one by one. Because of the substantial uniformity achieved among the individual sensing elements produced, only limited testing or screening is necessary in order to determine that all of the sensing elements produced meet product specifications. The sensing elements produced in accordance with the present invention have outstanding sensing characteristics and are provided in a form which is very convenient for inclusion in a sensor holder or fixture. Thus, the present invention advantageously makes sensing an analyte of interest, for example, a gas, in a medium, for example blood, more cost effective, convenient, and reliable.

Example 5

A 0.37 gm portion of a vinyl functional silicone (General Electric 1145-122) was mixed with a 0.45 gm portion of a silicon-hydride functional silicone (General Electric 1145-124). To this mixture was added 0.014 gm of a crosslinker/dye compound consisting of silyl-hydride covalently bonded to isobenzperylene. The formulation was thoroughly mixed to form a hydrosilylation cure silicone PSA and cast onto a release liner. The cast PSA sensing composition was 0.0051 cm thick. The cast film was held at 110° C. for 30 minutes at the end of which time a dry, tacky, uniform film resulted.

To the above PSA/sensor film was laminated a 0.0051 cm thick black teflon film. Individual sensing elements of 2 mm diameter were die cut from the laminate. The release liner was removed from the teflon/PSA sensor/release liner laminate, and the individual sensing element was placed into the well of a polycarbonate sensor holder. The sensing element adhered strongly to both the teflon layer and the polycarbonate sensor holder, and could be removed only with difficulty even after 45 days aging.

To demonstrate the ability of the sensing element to sense oxygen, a one square cm piece of the aforementioned laminate was placed into a gas flow-through cell and tested when exposed to a 0% oxygen (i.e., pure nitrogen) and a 10% oxygen atmosphere. Using a 390 nm excitation signal (generated by a Spex FluoroLog-2 fluorimeter), emission intensities at 420 nm were recorded. For the above sensing element the emission intensity at 0% $O_2$ was $1.98 \times 10^6$, and at 10% $O_2$ was $1.33 \times 10^6$. A slope of 0.007 $mm^{-1}$ was calculated for this sensing element which compares favorably to slopes found in typical non-adhesive $O_2$ sensors.

The above data illustrate that an adhesive sensing element can be fabricated. The PSA matrix is comprised of a crosslinked poly(dimethylsiloxane) and a tackifying resin. The PSA matrix bonds securely to both a sensor holder and an optical isolation barrier film. This provides a sensing element with very simple construction and eliminates the need for special coatings or treatments used to enhance the adhesion of traditional silicone matrices to sensor holders and/or optical barrier films.

While this invention has been described with respect to various specific examples and embodiments, it is to be understood that the invention is not limited thereto and it can be variously practiced within the scope of the following claims.

What is claimed is:

1. A method for making an optical sensor capable of sensing an analyte, which method comprises:
   continuously placing a sensing composition precursor comprising a sensing component and a polymeric precursor on a continuous web thereby forming a continuous precursor-containing web, wherein said continuous sensing composition is present as a layer having a substantially uniform thickness on said continuous web; and
   forming a continuous sensing composition responsive to the analyte from said sensing composition precursor included in said continuous precursor-containing web, thereby producing a sensing composition-containing web, said continuous sensing composition being sized and structured to be dividable among a plurality of uniform sensing elements.

2. The method of claim 1 wherein said continuous sensing composition is useful in sensing the concentration of a gas in a medium.

3. The method of claim 1 wherein said continuous web comprises a transparent material which is polymeric.

4. The method of claim 1 wherein said sensing composition precursor comprises a sensing component, a polymer precursor and an effective amount of a light activated polymerization catalyst component, and said forming comprises polymerizing said polymer precursor and includes exposing said sensing composition precursor to sufficient light energy to activate said light activated polymerization catalyst.

5. The method of claim 4 wherein said light exposing step is effective to partially polymerize said polymer precursor and said forming further includes exposing said partially polymerized polymer precursor to elevated temperature to further polymerize said partially polymerized polymer precursor.

6. The method of claim 1 wherein said sensing composition precursor comprises a sensing component, a polymer precursor and an effective amount of a polymerization catalyst component, and said forming comprises polymerizing said polymer precursor and includes exposing said sensing composition precursor to elevated temperature to facilitate said polymerization catalyst component in promoting polymerization.

7. The method of claim 1 wherein said continuous web is treated, or is coated, to enhance the adhesion of said sensing composition to said continuous web.

8. The method of claim 1 wherein said continuous web is a continuous opaque film permeable to the analyte.

9. The method of claim 1 which further comprises placing a continuous opaque film on said sensing composition, said continuous opaque film being permeable to the analyte.

10. The method of claim 1 which further comprises placing a continuous adhesive layer on said continuous web so that said continuous web is located between said continuous adhesive layer and said sensing composition, said continuous adhesive layer includes an adhesive composition and a non-adhesive release membrane in contact with said adhesive composition, said continuous adhesive layer being placed so that said adhesive composition is in contact with said continuous web and a layered composite is formed.

11. The method of claim 1 which further comprises forming a plurality of sensing elements from said sensing composition-containing web, each of said plurality of sensing elements including a sensing composition layer, and securing an individual sensing element formed from said sensing composition-containing web to a sensor fixture.

12. The method of claim 11 wherein each of said plurality of sensing elements includes no portion of said continuous web.

13. The method of claim 11 wherein said forming step includes removing said continuous web from said sensing composition-containing web.

14. The method of claim 10 which further comprises forming a plurality of sensing elements from said layered composite, each of said plurality of sensing elements including a sensing composition layer, a web layer and an adhesive layer, removing an individual sensing element from said non-adhesive release membrane, and securing said individual sensing element removed from said non-adhesive release membrane to a sensor fixture.

15. The method of claim 8, wherein said sensing composition comprises a pressure sensitive adhesive capable of securely adhering to a sensor holder and to said continuous web.

16. A method for making an optical sensor capable of sensing an analyte, which method comprises:
    placing a sensing composition precursor on a continuous web thereby forming a continuous precursor-containing web;
    forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements; and
    placing a continuous opaque layer or film on said continuous sensing composition, thereby forming a composite structure.

17. The method of claim 16 wherein said continuous sensing composition is useful in sensing the concentration of a gas in a medium, wherein said opaque film is formed by polymerizing an opaque film precursor comprising an opaque agent and a polymeric material precursor, and said continuous sensing composition and said continuous opaque film are present as layers each having a substantially uniform thickness.

18. The method of claim 16 which further comprises forming a plurality of sensing elements from said composite structure, each of said plurality of sensing elements including a sensing composition layer and an opaque film layer, and securing one of said sensing elements to a sensor fixture.

19. A method for making an optical sensor capable of sensing an analyte, which method comprises:
    providing a sensing composition precursor comprising a sensing component, a polymer precursor, and an effective amount of a light activated polymerization catalyst component; and
    forming a sensing composition responsive to the analyte from said sensing composition precursor, by exposing said sensing composition precursor to sufficient light energy to activate said light activated polymerization catalyst component and to partially polymerize said polymer precursor, and exposing said partially polymerized polymer precursor to elevated temperature to further polymerize said partially polymerized polymer precursor.

20. The method of claim 19 wherein said sensing composition is useful in sensing the concentration of a gas in a medium.

21. The method of claim 19 wherein said light energy is selected from the group consisting of visible light energy, ultraviolet light energy and mixtures thereof.

22. The method of claim 19 which further comprises securing a sensing element including at least a portion of said sensing composition to a sensor fixture.

23. A method for making an optical sensor capable of sensing an analyte, which method comprises:

placing a sensing composition precursor on a continuous web, thereby forming a continuous precursor-containing web;

forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and placing a continuous adhesive layer on said continuous web so that said continuous web is located between said continuous adhesive layer and said sensing composition thereby forming a layered composite.

24. The method of claim 23 wherein said continuous sensing composition is present as a substantially uniform layer on said continuous web and is useful in sensing the concentration of a gas in a medium.

25. The method of claim 23 wherein said continuous web comprises a material which is polymeric, said sensing composition precursor comprises a sensing component and a polymer precursor, and said forming comprises polymerizing said polymer precursor.

26. The method of claim 23 which further comprises forming a plurality of sensing elements from said layered composite, each of said plurality of sensing elements including a sensing composition layer, a web layer made of said continuous web and an adhesive layer including an adhesive composition and a non-adhesive release membrane in contact with said adhesive composition, said continuous adhesive layer being placed so that said adhesive composition is in contact with said continuous web, removing an individual sensing element from said non-adhesive release membrane, and securing said individual sensing element removed from said non-adhesive release membrane to a sensor fixture.

27. A method for making an optical sensor capable of sensing an analyte, which method comprises:

placing a sensing composition precursor on a continuous web, thereby forming a continuous precursor-containing web;

forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and wherein said sensing composition comprises: an aqueous first phase comprising a pH sensitive indicator component which is effective to provide a signal in response to the concentration of analyte in a medium to which said sensing composition is exposed, said analyte being effective to alter the pH of said primary phase; and a hydrophobic second phase which is permeable to said analyte and impermeable to ionized hydrogen, wherein said hydrophobic phase lies between said aqueous phase and said medium to which said sensing composition is exposed, wherein said sensing composition is substantially free of partitioning species other than the analyte of interest which can migrate from one phase to the other in response to a change in pH in said aqueous phase and which substantially affect said concentration dependent signal.

28. The method of claim 27 which further comprises forming a plurality of sensing elements from said layered composite, each of said plurality of sensing elements including a sensing composition layer, a web layer made of said continuous web and an adhesive layer including an adhesive composition and a non-adhesive release membrane in contact with said adhesive composition, said continuous adhesive layer being placed so that said adhesive composition is in contact with said continuous web, removing an individual sensing element from said non-adhesive release membrane, and securing said individual sensing element removed from said non-adhesive release membrane to a sensor fixture.

29. The method of claim 28, wherein said continuous web comprises polycarbonate, wherein said analyte is carbon dioxide, and wherein said pH sensitive indicator component comprises HPTS.

30. The method of claim 29, wherein said sensor, after being equilibrated in a medium having a $pCO_2$ of 0.25 mmHg, provides a signal which drifts less than 6% over a three hour period when moved from said medium to a medium having a $pCO_2$ of 45.6 mmHg.

31. A sensing composition-containing web comprising:

a continuous web;

a continuous sensing composition responsive to an analyte and located on said continuous web; and wherein the surface of said continuous web on which said continuous sensing composition is located being treated or coated so as to enhance the adhesion between said continuous web and said continuous sensing composition.

32. The sensing composition-containing web of claim 31 wherein said continuous sensing composition is present as a layer having a substantially uniform thickness and is sized and structured to be dividable among a plurality of sensing elements.

33. The sensing composition-containing web of claim 31 which further comprises a continuous opaque layer located on said continuous sensing composition, said continuous opaque layer being permeable to the analyte.

34. An article formed by continuously placing a sensing composition precursor on a continuous web thereby forming a continuous precursor-containing web;

placing a continuous adhesive layer on said continuous web so that said continuous web is located between said continuous adhesive layer and said sensing composition, said continuous adhesive layer includes an adhesive composition and a non-adhesive release membrane in contact with said adhesive composition, said continuous adhesive layer being placed so that said adhesive composition is in contact with said continuous web and a layered composite is formed; and forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements.

35. An article formed by continuously placing a sensing composition precursor on a continuous web thereby forming a continuous precursor-containing web, wherein said continuous web comprises a continuous opaque film permeable to the analyte;

forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements and wherein said sensing composition comprises a pressure sensitive adhesive capable of securely adhering to a sensor holder and to said continuous web.

36. A source of optical sensing elements comprising:

a continuous release membrane; and a plurality of optical sensing elements each of which is located on said continuous release membrane, each of said sensing elements comprising a sensing composition responsive to an analyte to be sensed by said sensing element.

37. The source of sensing elements of claim 36 wherein each of said sensing elements further comprises:

an adhesive composition in contact with said continuous release membrane; and a web layer in contact with said adhesive composition.

38. A sensing composition precursor comprising:

an indicator component responsive to an analyte;

a polymer precursor which, after polymerization, is effective as a matrix material for said indicator component; and a light activated polymerization catalyst component selected from the group consisting of cyclopentadienyl trimethyl platinum, derivatives thereof and mixtures thereof in an amount effective to promote polymerization of said polymer precursor after being activated by light energy.

39. The sensing composition precursor of claim 38 wherein said polymer precursor is a precursor of a vinyl/hydride addition cure polysiloxane polymer.

40. The sensing composition precursor of claim 38 wherein said light activated polymerization catalyst component is effective, after being activated by light energy, to promote further polymerization of said polymer precursor at elevated temperatures.

41. A sensor for measuring the concentration of an analyte in a medium comprising:

a sensing element produced by continuously placing a sensing composition precursor on a continuous web thereby forming a continuous precursor-containing web; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements; and forming a plurality of sensing elements from said sensing composition-containing web, each of said plurality of sensing elements including a sensing composition layer, and securing an individual sensing element formed from said sensing composition-containing web to a sensor fixture;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

42. A sensor for measuring the concentration of an analyte in a medium comprising:

a sensing element produced by continuously placing a sensing composition precursor on a continuous web thereby forming a continuous precursor-containing web; placing a continuous adhesive layer on said continuous web so that said continuous web is located between said continuous adhesive layer and said sensing composition, said continuous adhesive layer includes an adhesive composition and a non-adhesive release membrane in contact with said adhesive composition, said continuous adhesive layer being placed so that said adhesive composition is in contact with said continuous web and a layered composite is formed; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements and forming a plurality of sensing elements from said layered composite, each of said plurality of sensing elements including a sensing composition layer, a web layer and an adhesive layer, removing an individual sensing element from said non-adhesive release membrane, and securing said individual sensing element removed from said non-adhesive release membrane to a sensor fixture;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

43. A sensor for measuring the concentration of an analyte in a medium comprising:

a sensing element produced by placing a sensing composition precursor on a continuous web thereby forming a continuous precursor-containing web; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements; and placing a continuous opaque layer of film on said continuous sensing composition, thereby forming a composite structure, wherein said continuous sensing composition is useful in sensing the concentration of a gas in a medium, wherein said opaque film is formed by polymerizing an opaque film precursor comprising an opaque agent and a polymeric material precursor, and said continuous sensing composition and said continuous opaque film are present as layers each having a substantially uniform thickness;

an excitation assembly positioned and adapted to provide an excitation signal to said sensing element;

a detector assembly positioned and adapted to detect an emitted signal from said sensing element, said sensing element being capable of providing said emitted signal in response to being exposed to said excitation signal; and a processor assembly positioned and adapted to analyze said emitted signal in determining the concentration of said analyte in said medium.

44. A sensor for measuring the concentration of an analyte in a medium comprising:

a sensing element produced by providing a sensing composition precursor comprising a sensing component, a polymer precursor, and an effective amount of a light activated polymerization catalyst component; and forming a sensing composition responsive to the analyte from said sensing composition precursor, by exposing said sensing composition precursor to sufficient light energy to activate said light activated polymerization catalyst component and to partially polymerize said polymer precursor, and exposing said partially polymerized polymer precursor to elevated temperature to further polymerize said partially polymerized polymer precursor and securing a sensing element including at least a portion of said sensing composition to a sensor fixture;

an excitation assembly positioned and adapted to provide an excitation signal to said sensing element;

a detector assembly positioned and adapted to detect an emitted signal for said sensing element, said sensing element being capable of providing said emitted signal in response to being exposed to said excitation signal; and a processor assembly positioned and adapted to analyze said emitted signal in determining the concentration of said analyte in said medium.

45. A sensor for measuring the concentration of an analyte in a medium comprising:

a sensing element produced by placing a sensing composition precursor on a continuous web, thereby forming a continuous precursor-containing web; forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and placing a continuous adhesive layer on said continuous web so that said continuous web is located between said continuous adhesive layer and said sensing composition thereby forming a layered composite, wherein said continuous web comprises a material which is polymeric, said sensing composition precursor comprises a sensing component and a polymer precursor, and said forming comprises polymerizing said polymer precursor;

an excitation assembly positioned and adapted to provide an excitation signal to said sensing element;

a detector assembly positioned and adapted to provide an excitation signal to said sensing element;

a detector assembly positioned and adapted to detect an emitted signal for said sensing element, said sensing element being capable of providing said emitted signal in response to being exposed to said excitation signal; and a processor assembly positioned and adapted to analyze said emitted signal in determining the concentration of said analyte in said medium.

46. A sensor for measuring the concentration of an analyte in a medium comprising:

a sensing element produced by placing a sensing composition precursor on a continuous web, thereby forming a continuous precursor-containing web; forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and wherein said sensing composition comprises: an aqueous first phase comprising a pH sensitive indicator component which is effective to provide a signal in response to the concentration of analyte in a medium to which said sensing composition is exposed, said analyte being effective to alter the pH of said primary phase; and a hydrophobic second phase which is permeable to said analyte and impermeable to ionized hydrogen, wherein said hydrophobic phase lies between said aqueous phase and said medium to which said sensing composition is exposed, wherein said sensing composition is substantially free of partitioning species other than the analyte of interest which can migrate from one phase to the other in response to a change in pH in said aqueous phase and which substantially affect said concentration dependent signal; and forming a plurality of sensing elements from said layered composite, each of said plurality of sensing elements including a sensing composition layer, a web layer made of said continuous web and an adhesive layer including an adhesive composition and a non-adhesive release membrane in contact with said adhesive composition, said continuous adhesive layer being placed so that said adhesive composition is in contact with said continuous web, removing an individual sensing element from said non-adhesive release membrane, and securing said individual sensing element removed from said non-adhesive release membrane to a sensor fixture, wherein said continuous web comprises polycarbonate, wherein said analyte is carbon dioxide, and wherein said pH sensitive indicator component comprises HPTS:

an excitation assembly positioned and adapted to provide an excitation signal to said sensing element;

a detector assembly positioned and adapted to provide an excitation signal to said sensing element;

a detector assembly positioned and adapted to detect an emitted signal for said sensing element, said sensing element being capable of providing said emitted signal in response to being exposed to said excitation signal; and a processor assembly positioned and adapted to analyze said emitted signal in determining the concentration of said analyte in said medium.

47. A sensor comprising:

a sensor fixture including a surface adapted to be exposed to a medium containing an analyte the concentration of which is to be determined; and a sensing element produced by continuously placing a sensing composition precursor on a continuous web thereby forming a continuous precursor-containing web; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements; and forming a plurality of sensing elements from said sensing composition-containing web, each of said plurality of sensing elements including a sensing composition layer, and securing an individual sensing element formed from said sensing composition-containing web to a sensor fixture, secured to said sensor fixture, said sensing element being located relative to said surface so as to be exposed to said medium when said surface is so exposed.

48. The sensor of claim 47, wherein said sensor fixture includes a cavity and said sensing element is at least partially located in said cavity.

49. A sensor comprising:
a sensor fixture including a surface adapted to be exposed to a medium containing an analyte the concentration of which is to be determined; and
a sensing element produced by continuously placing a sensing composition precursor on a continuous web thereby forming a continuous precursor-containing web; placing a continuous adhesive layer on said continuous web so that said continuous web is located between said continuous adhesive layer and said sensing composition, said continuous adhesive layer includes an adhesive composition and a non-adhesive release membrane in contact with said adhesive composition, said continuous adhesive layer being placed so that said adhesive composition is in contact with said continuous web and a layered composite is formed; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements and forming a plurality of sensing elements from said layered composite, each of said plurality if sensing elements including a sensing composition layer, a web layer and an adhesive layer, removing an individual sensing element from said non-adhesive release membrane, and securing said individual sensing element removed from said non-adhesive release membrane to a sensor fixture, said sensing element being located relative to said surface so as to be exposed to said medium when said surface is so exposed.

50. The sensor of claim 49 wherein said sensor fixture includes a cavity and said sensing element is at least partially located in said cavity.

51. A sensor comprising:
a sensor fixture including a surface adapted to be exposed to a medium containing an analyte the concentration of which is to be determined; and
a sensing element produced by placing a sensing composition precursor on a continuous web thereby forming a continuous precursor-containing web; forming a continuous sensing composition responsive to the analyte from said sensing composition precursor included in said continuous precursor-containing web, thereby producing a sensing composition-containing web, said continuous sensing composition being sized and structured to be dividable among a plurality of sensing elements; and placing a continuous opaque layer or film on said continuous sensing composition, thereby forming a composite structure, wherein said continuous sensing composition is useful in sensing the concentration of a gas in a medium, wherein said opaque film is formed by polymerizing an opaque film precursor comprising an opaque agent and a polymeric material precursor, and said continuous sensing composition and said continuous opaque film are present as layers each having a substantially uniform thickness, secured to said sensor fixture, said sensing element being located relative to said surface so as to be exposed to said medium when said surface is so exposed.

52. The sensor of claim 51, wherein said sensor fixture includes a cavity and said sensing element is at least partially located in said cavity.

53. A sensor comprising:
a sensor fixture including a surface adapted to be exposed to a medium containing an analyte the concentration of which is to be determined; and
a sensing element produced by providing a sensing composition precursor comprising a sensing component, a polymer precursor, and an effective amount of a light activated polymerization catalyst component; and forming a sensing composition responsive to the analyte from said sensing composition precursor, by exposing said sensing composition precursor to sufficient light energy to activate said light activated polymerization catalyst component and to partially polymerize said polymer precursor, and exposing said partially polymerized polymer precursor to elevated temperature to further polymerize said partially polymerized polymer precursor, wherein said light energy is selected from the group consisting of visible light energy, ultraviolet light energy and mixtures thereof, secured to said sensor fixture, said sensing element being located relative to said surface so as to be exposed to said medium when said surface is so exposed.

54. The sensor of claim 53, wherein said sensor fixture includes a cavity and said sensing element is at least partially located in said cavity.

55. A sensor comprising:
a sensor fixture including a surface adapted to be exposed to a medium containing an analyte the concentration of which is to be determined; and
a sensing element produced by placing a sensing composition precursor on a continuous web, thereby forming a continuous precursor-containing web; forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and placing a continuous adhesive layer on said continuous web so that said continuous web is located between said continuous adhesive layer and said sensing composition thereby forming a layered composite, wherein said continuous web comprises a material which is polymeric, said sensing composition precursor comprises a sensing component and a polymer precursor, and said forming comprises polymerizing said polymer precursor, secured to said sensor fixture, said sensing element being located relative to said surface so as to be exposed to said medium when said surface is so exposed.

56. The sensor of claim 55, wherein said sensor fixture includes a cavity and said sensing element is at least partially located in said cavity.

57. A sensor comprising:

a sensor fixture including a surface adapted to be exposed to a medium containing an analyte the concentration of which is to be determined; and a sensing element produced by placing a sensing composition precursor on a continuous web, thereby forming a continuous precursor-containing web; forming a continuous sensing composition responsive to the analyte from said sensing composition precursor included in said continuous precursor-containing web, thereby providing a sensing composition-containing web, said continuous sensing composition being sized and structured to be dividable among a plurality of sensing elements; and wherein said sensing composition comprises: an aqueous first phase comprising a pH sensitive indicator component which is effective to provide a signal in response to the concentration of analyte in a medium to which said sensing composition is exposed, said analyte being effective to alter the pH of said primary phase; and a hydrophobic second phase which is permeable to said analyte and impermeable to ionized hydrogen, wherein said hydrophobic phase lies between said aqueous phase and said medium to which said sensing composition is exposed, wherein said sensing composition is substantially free of partitioning species other than the analyte of interest which can migrate from one phase to the other in response to a change in pH in said aqueous phase and which substantially affect said concentration dependent signal; and forming a plurality of sensing elements from said layered composite; each of said plurality of sensing elements including a sensing composition layer, a web layer made of said continuous web and an adhesive layer including an adhesive composition and a non-adhesive release membrane in contact with said adhesive composition, said continuous adhesive layer being placed so that said adhesive composition is in contact with said continuous web, removing an individual sensing element from said non-adhesive release membrane, and securing said individual sensing element removed from said non-adhesive release membrane to a sensor fixture, wherein said continuous web comprises polycarbonate, wherein said analyte is carbon dioxide, and wherein said pH sensitive indicator component comprises HPTS, secured to said sensor fixture, said sensing element being located relative to said surface so as to be exposed to said medium when said surface is so exposed.

58. The sensor of claim 57, wherein said sensor fixture includes a cavity and said sensing element is at least partially located in said cavity.

* * * * *